(12) United States Patent
Zhang et al.

(10) Patent No.: US 8,569,569 B2
(45) Date of Patent: Oct. 29, 2013

(54) ULTRATHIN FLUID-ABSORBENT CORES

(75) Inventors: Xiaomin Zhang, Charlotte, NC (US);
Olaf Hoeller, Charlotte, NC (US);
Kathleen Goebel, Charlotte, NC (US)

(73) Assignee: BASF SE, Ludwigshafen (DE)

( * ) Notice: Subject to any disclaimer, the term of this patent is extended or adjusted under 35 U.S.C. 154(b) by 237 days.

(21) Appl. No.: 13/053,929

(22) Filed: Mar. 22, 2011

(65) Prior Publication Data

US 2011/0238026 A1    Sep. 29, 2011

Related U.S. Application Data

(60) Provisional application No. 61/316,879, filed on Mar. 24, 2010.

(51) Int. Cl.
*A61F 13/15* (2006.01)

(52) U.S. Cl.
USPC ............ 604/372; 604/368; 604/367; 604/374

(58) Field of Classification Search
USPC .................................. 604/372, 368, 367, 374
See application file for complete search history.

(56) References Cited

U.S. PATENT DOCUMENTS

| | | | |
|---|---|---|---|
| 5,269,980 A | 12/1993 | Levendis et al. | |
| 6,972,011 B2 | 12/2005 | Maeda et al. | |
| 2003/0181115 A1 | 9/2003 | Nagasuna et al. | |
| 2005/0137085 A1 | 6/2005 | Zhang et al. | |
| 2006/0004336 A1* | 1/2006 | Zhang et al. | 604/368 |
| 2006/0121814 A1* | 6/2006 | Vinson et al. | 442/417 |
| 2006/0217508 A1 | 9/2006 | Schmid et al. | |
| 2007/0100115 A1 | 5/2007 | Schmid et al. | |
| 2007/0135785 A1 | 6/2007 | Qin et al. | |
| 2007/0156108 A1 | 7/2007 | Becker et al. | |
| 2008/0125735 A1 | 5/2008 | Busam et al. | |
| 2008/0188586 A1 | 8/2008 | Bruhns et al. | |
| 2008/0188821 A1 | 8/2008 | Losch et al. | |
| 2009/0192035 A1 | 7/2009 | Stueven et al. | |
| 2009/0239071 A1 | 9/2009 | Stueven et al. | |
| 2009/0258994 A1 | 10/2009 | Stueven et al. | |
| 2009/0315204 A1 | 12/2009 | Losch et al. | |
| 2010/0010176 A1 | 1/2010 | Losch et al. | |
| 2010/0029866 A1 | 2/2010 | Losch et al. | |
| 2010/0068520 A1 | 3/2010 | Stueven | |

FOREIGN PATENT DOCUMENTS

| | | |
|---|---|---|
| DE | 103 14 466 A1 | 10/2004 |
| DE | 103 40 253 A1 | 3/2005 |
| DE | 10 2004 024 437 A1 | 12/2005 |
| DE | 10 2005 002 412 A1 | 7/2006 |
| EP | 0 348 180 A2 | 12/1989 |

(Continued)

OTHER PUBLICATIONS

Buchholz, Fredric L., et al., *Modern Superabsorbent Polymer Technology*, "Commercial Processes for the Manufacture of Superabsorbent Polymers," pp. 252-258, pp. 71-103. New York: John Wiley & Sons, Inc., 1998.

*Primary Examiner* — Jacqueline F. Stephens
(74) *Attorney, Agent, or Firm* — Marshall, Gerstein & Borun LLP

(57) ABSTRACT

The present invention relates to ultrathin fluid-absorbent cores comprising a substrate layer, water-absorbent polymer particles and an adhesive, wherein the wet SAP shake out of water-absorbent polymer particles out of the fluid-absorbent core is less than 10% by weight.

14 Claims, 9 Drawing Sheets

(56) References Cited

FOREIGN PATENT DOCUMENTS

| | | |
|---|---|---|
| EP | 1293187 A1 | 3/2003 |
| EP | 1447066 A1 | 8/2004 |
| EP | 1447067 A1 | 8/2004 |
| EP | 1609448 A1 | 12/2005 |
| JP | 2004/313580 A | 11/2004 |
| WO | WO-96/40427 A1 | 12/1996 |
| WO | WO-2004071363 A1 | 8/2004 |
| WO | WO-2005097025 A1 | 10/2005 |
| WO | WO-2006/079631 A1 | 8/2006 |
| WO | WO-2008/009580 A1 | 1/2008 |
| WO | WO-2008/009598 A1 | 1/2008 |
| WO | WO-2008/009599 A1 | 1/2008 |
| WO | WO-2008/009612 A1 | 1/2008 |
| WO | WO-2008/040715 A2 | 4/2008 |
| WO | WO-2008/052971 A1 | 5/2008 |
| WO | WO-2008086976 A1 | 7/2008 |
| WO | WO-2008155699 A1 | 12/2008 |
| WO | WO-2008155701 A2 | 12/2008 |
| WO | WO-2008155702 A1 | 12/2008 |
| WO | WO-2008155710 A1 | 12/2008 |
| WO | WO-2008155711 A1 | 12/2008 |
| WO | WO-2008155722 A2 | 12/2008 |

* cited by examiner

ULTRATHIN FLUID-ABSORBENT CORES

CROSS-REFERENCE TO RELATED APPLICATIONS

This application claims the benefit of U.S. provisional patent application No. 61/316,879, filed Mar. 24, 2010, incorporated herein by reference in its entirety.

The present invention relates to ultrathin fluid-absorbent cores comprising a substrate layer, water-absorbent polymer particles and an adhesive, wherein the wet SAP shake out (SAPLoss) of water-absorbent polymer particles out of the fluid-absorbent core is less than 10% by weight.

The production of fluid-absorbent articles is described in the monograph "Modern Superabsorbent Polymer Technology", F. L. Buchholz and A. T. Graham, Wiley-VCH, 1998, pages 252 to 258.

Fluid-absorbent articles such as disposable diapers typically comprise an upper liquid-pervious layer, a lower liquid-impervious layer, and a fluid-absorbent core between the upper and the lower layer. The fluid-absorbent cores typically comprise water-absorbent polymers and fibers.

Ultrathin fluid absorbent cores can be formed by immobilization of water-absorbent polymer particles on a nonwoven using hotmelt adhesives, i.e. forming longitudinal strips or discrete spots. Other patterns of the water-absorbent polymer particles are also possible.

The preparation of ultrathin fluid-absorbent cores is described, for example, in EP 1 293 187 A1, U.S. Pat. No. 6,972,011, EP 1 447 066 A1, EP 1 447 067 A1, EP 1 609 448 A1, JP 2004/313580, US 2005/0137085, US 2006/0004336, US 2007/135785 WO 2008/155699 A1, WO 2008/155701 A2, WO 2008/155702 A1, WO 2008/155710 A1, WO 2008/155711 A1, WO 2004/071363 A1, US 2003/0181115, WO 2005/097025, US 2007/156108, US 2008/0125735, and WO 2008/155722 A2.

The production of water-absorbent polymer particles is likewise described in the monograph "Modern Superabsorbent Polymer Technology", F. L. Buchholz and A. T. Graham, Wiley-VCH, 1998, pages 71 to 103. Water-absorbent polymer particles are also referred to as "superabsorbent polymers" or "superabsorbents".

The preparation of water-absorbent polymer particles by polymerizing droplets of a monomer solution ("dropletization polymerization") is described, for example, in EP 0 348 180 A1, WO 96/40427 A1, U.S. Pat. No. 5,269,980, DE 103 14 466 A1, DE 103 40 253 A1, DE 10 2004 024 437 A1, DE 10 2005 002 412 A1, DE 10 2006 001 596 A1, WO 2008/009580 A1, WO 2008/009598 A1, WO 2008/009599 A1, WO 2008/009612 A1, WO 2008/040715 A2, WO 2008/052971, and WO 2008/086976 A1.

It was an object of the present invention to provide ultrathin fluid-absorbent cores having improved properties, i.e. a reduced wet SAP shake out (SAPLoss) of water-absorbent polymer particles.

The object is achieved by fluid-absorbent cores comprising a substrate layer, at least 75% by weight of water-absorbent polymer particles, and an adhesive, wherein the water-absorbent polymer particles have a mean sphericity from 0.86 to 0.99 and the wet SAP shake out (SAPLoss) of water-absorbent polymer particles out of the fluid-absorbent core is less than 10% by weight.

The fluid-absorbent core comprises preferably at least 80% by weight, more preferably at least 83% by weight, most preferably at least 85% by weight, of water-absorbent polymer particles.

The fluid-absorbent core comprises preferably not more than 15% by weight, more preferably not more than 10% by weight, most preferably not more than 7% by weight, of the adhesive.

In a preferred embodiment of the present invention a pressure sensitive adhesive is used that means that no solvent, water or heat is needed to activate the adhesive. The substrate layer is preferably a nonwoven layer or a tissue paper. Further, the fluid-absorbent cores can comprise two or more layers of water-absorbent polymer particles. The water-absorbent polymer particles are preferably placed in discrete regions of the fluid-absorbent core.

The wet SAP shake out (SAPLoss) of water-absorbent polymer particles out of the fluid-absorbent core is preferably less than 8% by weight, more preferably less than 6% by weight, most preferably less than 5% by weight.

The present invention is based on the finding that the wet SAP shake out (SAPLoss) of water-absorbent polymer particles can be reduced by using water-absorbent polymer particles having a specified shape and an adhesive. The water-absorbent polymer particles useful for fluid-absorbent cores according to the present invention are preferably prepared by dropletization polymerization.

The water-absorbent polymer particles have a mean sphericity of preferably from 0.87 to 0.97, more preferably from 0.88 to 0.95, most preferably from 0.89 to 0.93.

The water-absorbent polymer particles have a bulk density preferably at least 0.6 g/cm$^3$, more preferably at least 0.65 g/cm$^3$, most preferably at least 0.7 g/cm$^3$, and typically less than 1 g/cm$^3$.

The average particle diameter of the water-absorbent particles is preferably from 250 to 550 µm, more preferably from 350 to 500 µm, most preferably from 400 to 450 µm.

The particle diameter distribution is preferably less than 0.7, more preferably less than 0.65, more preferably less than 0.6.

The ratio of particles having one cavity to particles having more than one cavity is preferably less than 1.0, more preferably less than 0.7, most preferably less than 0.4. Lower ratios correlated with higher bulk densities.

Preferred water-absorbent polymer particles are polymer particles having a centrifuge retention capacity (CRC) of at least 30 g/g, preferably of at least 32 g/g, more preferably of at least 33 g/g, most preferably of at least 34 g/g, an absorption under high load (AUHL) of at least 15 g/g, preferably of at least 20 g/g, more preferably of at least 22 g/g, most preferably of at least 24 g/g, and a saline flow conductivity (SFC) of at least $5\times10^{-7}$ cm$^3$ s/g, preferably of at least $8\times10^{-7}$ cm$^3$ s/g, more preferably of at least $10\times10^{-7}$ cm$^3$ s/g, most preferably of at least $12\times10^{-7}$ cm$^3$ s/g.

Also preferred water-absorbent polymer particles are polymer particles having a centrifuge retention capacity (CRC) of at least 20 g/g, preferably of at least 24 g/g, more preferably of at least 26 g/g, most preferably of at least 28 g/g, an absorption under high load (AUHL) of at least 15 gig, preferably of at least 17 g/g, more preferably of at least 19 g/g, most preferably of at least 20 g/g, and a saline flow conductivity (SFC) of at least $80\times10^{-7}$ cm$^3$ s/g, preferably of at least $110\times10^{-7}$ cm$^3$ s/g, more preferably of at least $130\times10^{-7}$ cm$^2$ s/g, most preferably of at least $150\times10^{-7}$ cm$^3$ s/g.

Also preferred water-absorbent polymer particles are polymer particles having a centrifuge retention capacity (CRC) of at least 20 g/g, preferably of at least 24 g/g, more preferably of at least 26 g/g, most preferably of at least 28 g/g, and a free swell gel bed permeability (GBP) of at least 20 Darcies, preferably of at least 23 Darcies, more preferably of at least 25 Darcies, most preferably of at least 28 Darcies.

The present invention further provides fluid-absorbent articles which comprise the inventive fluid-absorbent cores.

DETAILED DESCRIPTION OF THE INVENTION

A. Definitions

Figure 1:
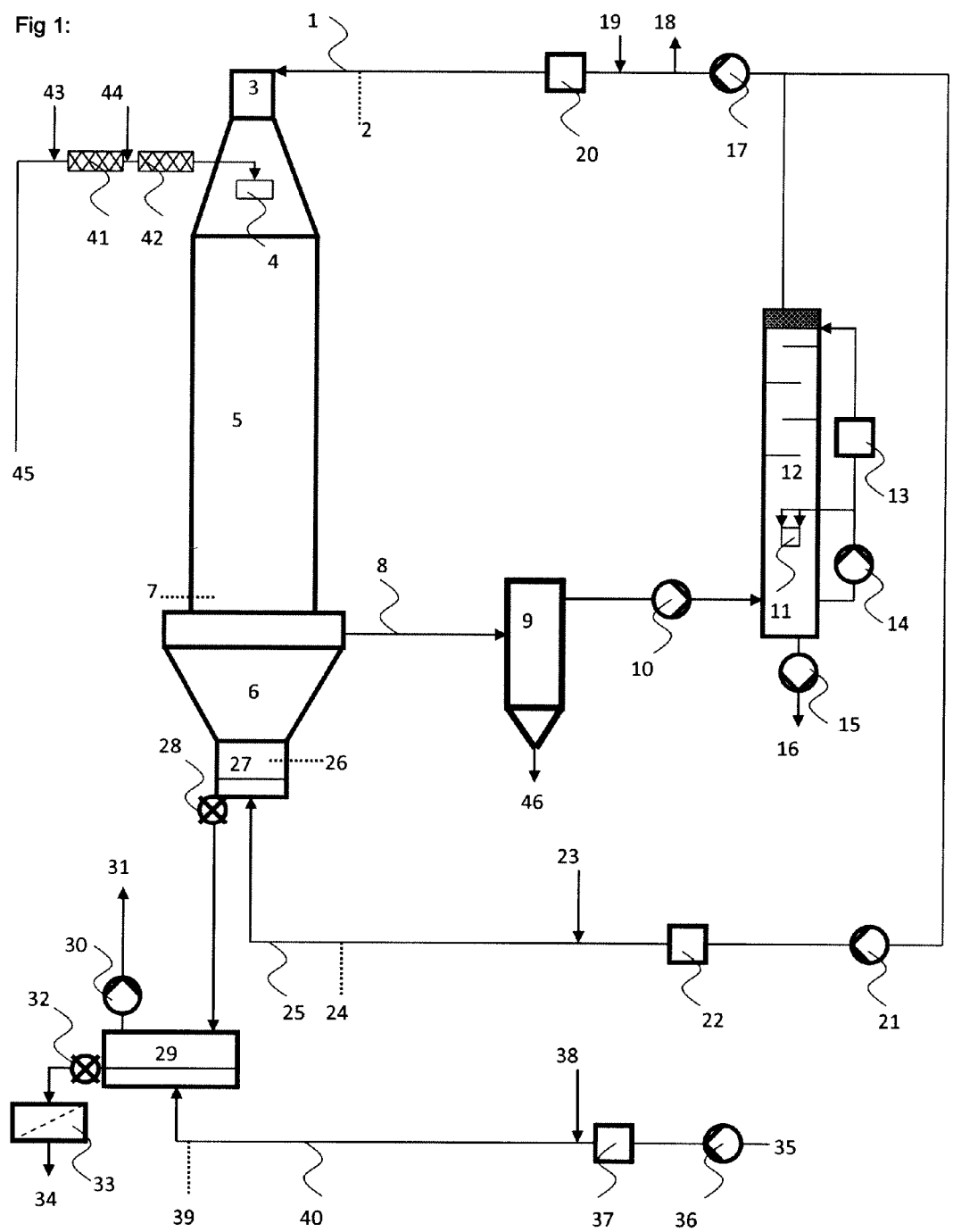
FIG. 1 illustrates a process scheme with external fluidized bed.
Figure 2:
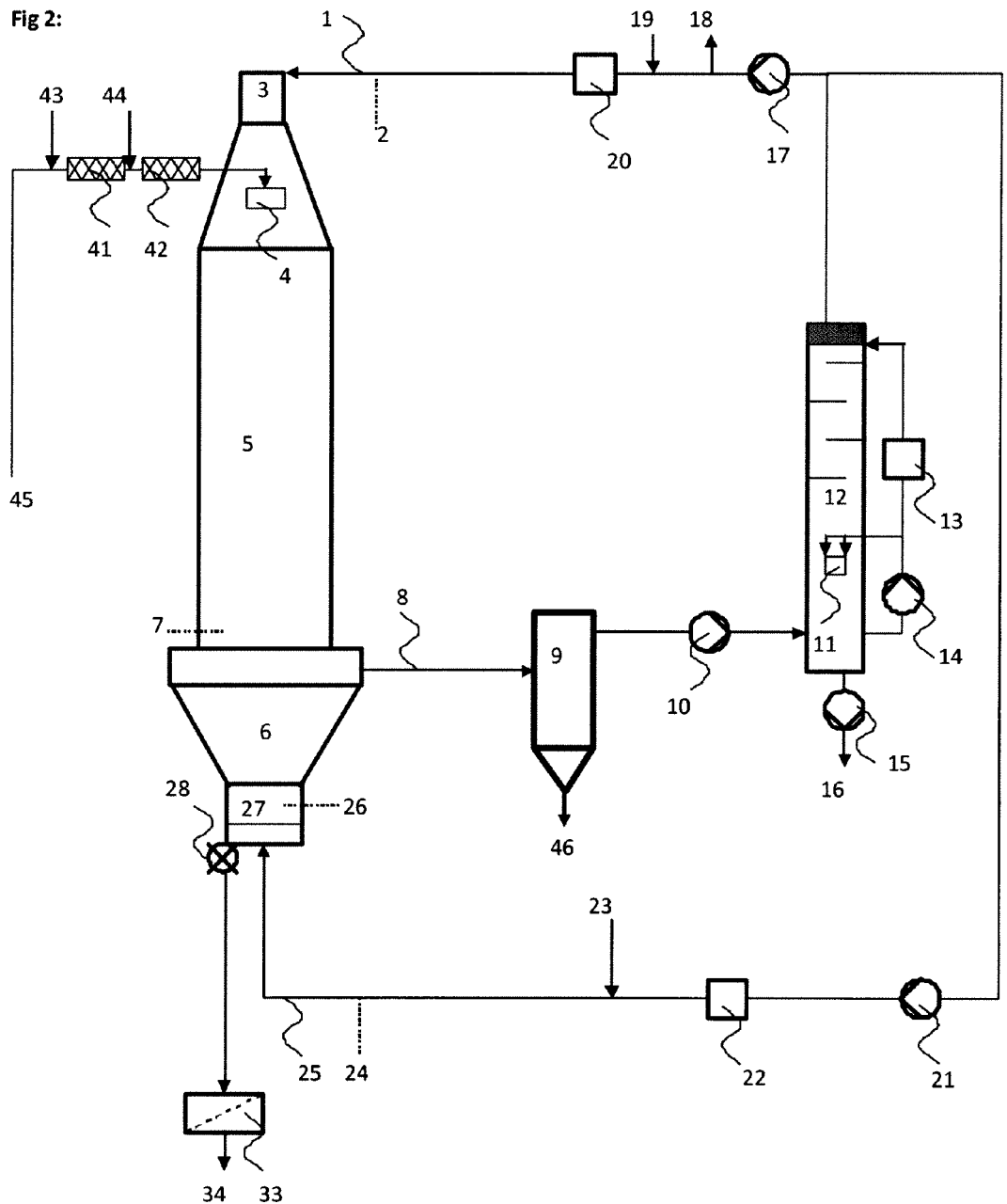
FIG. 2 illustrates a process scheme without external fluidized bed.

As used herein, the term "fluid-absorbent composition" refers to a component of the fluid-absorbent article which is primarily responsible for the fluid handling of the fluid-absorbent article including acquisition, transport, distribution and storage of body fluids.

As used herein, the term "fluid-absorbent core" refers to a fluid-absorbent composition comprising a fibrous material and water-absorbent polymer particles. The fluid-absorbent core is primarily responsible for the fluid handling of the fluid-absorbent article including acquisition, transport, distribution and storage of body fluids.

As used herein, the term "layer" refers to a fluid-absorbent composition whose primary dimension is along its length and width. It should be known that the term "layer" is not necessarily limited to single layers or sheets of the fluid-absorbent composition. Thus a layer can comprise laminates, composites, combinations of several sheets or webs of different materials.

As used herein, the term "x-dimension" refers to the length, and the term "y-dimension" refers to the width of the fluid-absorbent composition, layer, core or article. Generally, the term "x-y dimension" refers to the plane, orthogonal to the height or thickness of the fluid-absorbent composition, layer, core or article.

As used herein, the term "z-dimension" refers to the dimension orthogonal to the length and width of the fluid-absorbent composition, layer, core or article. Generally, the term "z-dimension" refers to the height of the fluid-absorbent composition.

As used herein, the term "chassis" refers to fluid-absorbent material comprising the upper liquid-pervious layer and the lower liquid-impervious layer.

As used herein, the term "basis weight" indicates the weight of the fluid-absorbent core per square meter and it includes the chassis of the fluid-absorbent article. The basis weight is determined at discrete regions of the fluid-absorbent core: the front overall average is the basis weight of the fluid-absorbent core 5.5 cm forward of the center of the core to the front distal edge of the core; the insult zone is the basis weight of the fluid-absorbent core 5.5 cm forward and 0.5 cm backwards of the center of the core; the back overall average is the basis weight of the fluid-absorbent core 0.5 cm backward of the center of the core to the rear distal edge of the core.

As used herein, the term "density" indicates the weight of the fluid-absorbent core per volume and it includes the chassis of the fluid-absorbent article. The density is determined at discrete regions of the fluid-absorbent core: the front overall average is the density of the fluid-absorbent core 5.5 cm forward of the center of the core to the front distal edge of the core; the insult zone is the density of the fluid-absorbent core 5.5 cm forward and 0.5 cm backwards of the center of the core; the back overall average is the density of the fluid-absorbent core 0.5 cm backward of the center of the core to the rear distal edge of the core.

Further, it should be understood, that the term "upper" refers to fluid-absorbent compositions which are nearer to the wearer of the fluid-absorbent article. Generally, the topsheet is the nearest composition to the wearer of the fluid-absorbent article, hereinafter described as "upper liquid-pervious layer". Contrarily, the term "lower" refers to fluid-absorbent compositions which are away from the wearer of the fluid-absorbent article. Generally, the backsheet is the composition which is furthermost away from the wearer of the fluid-absorbent article, hereinafter described as "lower liquid-impervious layer".

As used herein, the term "liquid-pervious" refers to a substrate, layer or laminate thus permitting liquids, i.e. body fluids such as urine, menses and/or vaginal fluids to readily penetrate through its thickness.

As used herein, the term "liquid-impervious" refers to a substrate, layer or a laminate that does not allow body fluids to pass through in a direction generally perpendicular to the plane of the layer at the point of liquid contact under ordinary use conditions.

Fluid-absorbent articles comprising more than one fluid-absorbent core, in a preferred manner comprising a double-core system including an upper core and a lower core, hereinafter called "primary core" and "secondary core".

As used herein, the term "hydrophilic" refers to the wettability of fibers by water deposited on these fibers. The term "hydrophilic" is defined by the contact angle and surface tension of the body fluids. According to the definition of Robert F. Gould in the 1964 American Chemical Society publication "Contact angle, wettability and adhesion", a fiber is referred to as hydrophilic, when the contact angle between the liquid and the fiber, especially the fiber surface, is less than 90° or when the liquid tends to spread spontaneously on the same surface.

Contrarily, "hydrophobic" refers to fibers showing a contact angle of greater than 90° or no spontaneously spreading of the liquid across the surface of the fiber.

As used herein, the term "section" or "zone" refers to a definite region of the fluid-absorbent composition.

As used herein, the term "article" refers to any three-dimensional solid material being able to acquire and store fluids discharged from the body. Preferred articles according to the present invention are disposable fluid-absorbent articles that are designed to be worn in contact with the body of a user such as disposable fluid-absorbent pantiliners, sanitary napkins, catamenials, incontinence inserts/pads, diapers, training pant diapers, breast pads, interlabial inserts/pads and the like.

As used herein, the term "body fluids" refers to any fluid produced and discharged by human or animal body, such as urine, menstrual fluids, faeces, vaginal secretions and the like.

B. Water-Absorbent Polymer Particles

The water-absorbent polymer particles are preferably prepared by polymerizing droplets of a monomer solution comprising
a) at least one ethylenically unsaturated monomer which bears acid groups and may be at least partly neutralized,
b) at least one crosslinker,
c) at least one initiator,
d) optionally one or more ethylenically unsaturated monomers copolymerizable with the monomers mentioned under a),
e) optionally one or more water-soluble polymers, and
f) water, in a surrounding heated gas phase and flowing the gas cocurrent through the polymerization chamber, wherein the temperature of the gas leaving the polymerization chamber is from 90 to 150° C., the gas velocity inside the polymerization chamber is from 0.1 to 2.5 m/s, and the droplets are generated by using a droplet plate having a multitude of bores.

The water-absorbent polymer particles are typically insoluble but swellable in water.

The monomers a) are preferably water-soluble, i.e. the solubility in water at 23° C. is typically at least 1 g/100 g of water, preferably at least 5 g/100 g of water, more preferably at least 25 g/100 g of water, most preferably at least 35 g/100 g of water.

Suitable monomers a) are, for example, ethylenically unsaturated carboxylic acids such as acrylic acid, methacrylic acid, maleic acid, and itaconic acid. Particularly preferred monomers are acrylic acid and methacrylic acid. Very particular preference is given to acrylic acid.

Further suitable monomers a) are, for example, ethylenically unsaturated sulfonic acids such as vinylsulfonic acid, styrenesulfonic acid and 2-acrylamido-2-methylpropanesulfonic acid (AMPS).

Impurities may have a strong impact on the polymerization. Preference is given to especially purified monomers a). Useful purification methods are disclosed in WO 2002/055469 A1, WO 2003/078378 A1 and WO 2004/035514 A1. A suitable monomer a) is according to WO 2004/035514 A1 purified acrylic acid having 99.8460% by weight of acrylic acid, 0.0950% by weight of acetic acid, 0.0332% by weight of water, 0.0203 by weight of propionic acid, 0.0001% by weight of furfurals, 0.0001% by weight of maleic anhydride, 0.0003% by weight of diacrylic acid and 0.0050% by weight of hydroquinone monomethyl ether.

Polymerized diacrylic acid is a source for residual monomers due to thermal decomposition. If the temperatures during the process are low, the concentration of diacrylic acid is no more critical and acrylic acids having higher concentrations of diacrylic acid, i.e. 500 to 10,000 ppm, can be used.

The content of acrylic acid and/or salts thereof in the total amount of monomers a) is preferably at least 50 mol %, more preferably at least 90 mol %, most preferably at least 95 mol %.

The acid groups of the monomers a) are typically partly neutralized, preferably to an extent of from 25 to 85 mol %, preferentially to an extent of from 50 to 80 mol %, more preferably from 60 to 75 mol %, for which the customary neutralizing agents can be used, preferably alkali metal hydroxides, alkali metal oxides, alkali metal carbonates or alkali metal hydrogen carbonates, and mixtures thereof. Instead of alkali metal salts, it is also possible to use ammonia or organic amines, for example, triethanolamine. It is also possible to use oxides, carbonates, hydrogencarbonates and hydroxides of magnesium, calcium, strontium, zinc or aluminum as powders, slurries or solutions and mixtures of any of the above neutralization agents. Examples for a mixture is a solution of sodiumaluminate. Sodium and potassium are particularly preferred as alkali metals, but very particular preference is given to sodium hydroxide, sodium carbonate or sodium hydrogen carbonate, and mixtures thereof. Typically, the neutralization is achieved by mixing in the neutralizing agent as an aqueous solution, as a melt or preferably also as a solid. For example, sodium hydroxide with water content significantly below 50% by weight may be present as a waxy material having a melting point above 23° C. In this case, metered addition as piece material or melt at elevated temperature is possible.

Optionally, it is possible to add to the monomer solution, or to starting materials thereof, one or more chelating agents for masking metal ions, for example iron, for the purpose of stabilization. Suitable chelating agents are, for example, alkali metal citrates, citric acid, alkali metal tatrates, alkali metal lactates and glycolates, pentasodium triphosphate, ethylenediamine tetraacetate, nitrilotriacetic acid, and all chelating agents known under the Trilon® name, for example Trilon® C (pentasodium diethylenetriaminepentaacetate), Trilon® D (trisodium (hydroxyethyl)-ethylenediaminetriacetate), and Trilon® M (methylglycinediacetic acid).

The monomers a) comprise typically polymerization inhibitors, preferably hydroquinone monoethers, as inhibitor for storage.

The monomer solution comprises preferably up to 250 ppm by weight, more preferably not more than 130 ppm by weight, most preferably not more than 70 ppm by weight, preferably not less than 10 ppm by weight, more preferably not less than 30 ppm by weight and especially about 50 ppm by weight of hydroquinone monoether, based in each case on acrylic acid, with acrylic acid salts being counted as acrylic acid. For example, the monomer solution can be prepared using acrylic acid having appropriate hydroquinone monoether content. The hydroquinone monoethers may, however, also be removed from the monomer solution by absorption, for example on activated carbon.

Preferred hydroquinone monoethers are hydroquinone monomethyl ether (MEHQ) and/or alpha-tocopherol (vitamin E).

Suitable crosslinkers b) are compounds having at least two groups suitable for crosslinking. Such groups are, for example, ethylenically unsaturated groups which can be polymerized by a free-radical mechanism into the polymer chain and functional groups which can form covalent bonds with the acid groups of monomer a). In addition, polyvalent metal ions which can form coordinate bond with at least two acid groups of monomer a) are also suitable crosslinkers b).

The crosslinkers b) are preferably compounds having at least two free-radically polymerizable groups which can be polymerized by a free-radical mechanism into the polymer network. Suitable crosslinkers b) are, for example, ethylene glycol dimethacrylate, diethylene glycol diacrylate, polyethylene glycol diacrylate, allyl methacrylate, trimethylolpropane triacrylate, triallylamine, tetraallylammonium chloride, tetraallyloxyethane, as described in EP 0 530 438 A1, di- and triacrylates, as described in EP 0 547 847 A1, EP 0 559 476 A1, EP 0 632 068 A1, WO 93/21237 A1, WO 2003/104299 A1, WO 2003/104300 A1, WO 2003/104301 A1 and in DE 103 31 450 A1, mixed acrylates which, as well as acrylate groups, comprise further ethylenically unsaturated groups, as described in DE 103 314 56 A1 and DE 103 55 401 A1, or crosslinker mixtures, as described, for example, in DE 195 43 368 A1, DE 196 46 484 A1, WO 90/15830 A1 and WO 2002/32962 A2.

Suitable crosslinkers b) are in particular pentaerythritol triallyl ether, tetraallyloxyethane, N,N'-methylenebisacrylamide, 15-tuply ethoxylated trimethylolpropane, polyethylene glycol diacrylate, trimethylolpropane triacrylate and triallylamine.

Very particularly preferred crosslinkers b) are the polyethoxylated and/or -propoxylated glycerols which have been esterified with acrylic acid or methacrylic acid to give di- or triacrylates, as described, for example in WO 2003/104301 A1. Di- and/or triacrylates of 3- to 10-tuply ethoxylated glycerol are particularly advantageous. Very particular preference is given to di- or triacrylates of 1- to 5-tuply ethoxylated and/or propoxylated glycerol. Most preferred are the triacrylates of 3- to 5-tuply ethoxylated and/or propoxylated glycerol and especially the triacrylate of 3-tuply ethoxylated glycerol.

The amount of crosslinker b) is preferably from 0.05 to 1.5% by weight, more preferably from 0.1 to 1% by weight, most preferably from 0.3 to 0.6% by weight, based in each case on monomer a). On increasing the amount of crosslinker b) the centrifuge retention capacity (CRC) decreases and the absorption under a pressure of 21.0 g/cm$^2$ (AUL) passes through a maximum.

The initiators c) used may be all compounds which disintegrate into free radicals under the polymerization conditions, for example peroxides, hydroperoxides, hydrogen peroxide, persulfates, azo compounds and redox initiators. Preference is given to the use of water-soluble initiators. In some cases, it is advantageous to use mixtures of various initiators, for example mixtures of hydrogen peroxide and sodium or potassium peroxodisulfate. Mixtures of hydrogen peroxide and sodium peroxodisulfate can be used in any proportion.

Particularly preferred initiators c) are azo initiators such as 2,2'-azobis[2-(2-imidazolin-2-yl)propane]dihydrochloride and 2,2'-azobis[2-(5-methyl-2-imidazolin-2-yl)propane]dihydrochloride, and photoinitiators such as 2-hydroxy-2-methylpropiophenone and 1-[4-(2-hydroxyethoxy)phenyl]-2-hydroxy-2-methyl-1-propan-1-one, redox initiators such as sodium persulfate/hydroxymethylsulfinic acid, ammonium peroxodisulfate/hydroxymethylsulfinic acid, hydrogen peroxide/hydroxymethylsulfinic acid, sodium persulfate/ascorbic acid, ammonium peroxodisulfate/ascorbic acid and hydrogen peroxide/ascorbic acid, photoinitiators such as 1-[4-(2-hydroxyethoxy)phenyl]-2-hydroxy-2-methyl-1-propan-1-one, and mixtures thereof. The reducing component used is, however, preferably a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The initiators are used in customary amounts, for example in amounts of from 0.001 to 5% by weight, preferably from 0.01 to 2% by weight, based on the monomers a).

Examples of ethylenically unsaturated monomers c) which are copolymerizable with the monomers a) are acrylamide, methacrylamide, hydroxyethyl acrylate, hydroxyethyl methacrylate, dimethylaminoethyl acrylate, dimethylaminoethyl methacrylate, dimethylaminopropyl acrylate and diethylaminopropyl methacrylate.

Useful water-soluble polymers d) include polyvinyl alcohol, polyvinylpyrrolidone, starch, starch derivatives, modified cellulose such as methylcellulose or hydroxyethylcellulose, gelatin, polyglycols or polyacrylic acids, polyesters and polyamides, polylactic acid, polyvinylamine, preferably starch, starch derivatives and modified cellulose.

For optimal action, the preferred polymerization inhibitors require dissolved oxygen. Therefore, the monomer solution can be freed of dissolved oxygen before the polymerization by inertization, i.e. flowing through with an inert gas, preferably nitrogen. It is also possible to reduce the concentration of dissolved oxygen by adding a reducing agent. The oxygen content of the monomer solution is preferably lowered before the polymerization to less than 1 ppm by weight, more preferably to less than 0.5 ppm by weight.

The water content of the monomer solution is preferably less than 65% by weight, preferentially less than 62% by weight, more preferably less than 60% by weight, most preferably less than 58% by weight.

The monomer solution has, at 20° C., a dynamic viscosity of preferably from 0.002 to 0.02 Pa·s, more preferably from 0.004 to 0.015 Pa·s, most preferably from 0.005 to 0.01 Pa·s. The mean droplet diameter in the droplet generation rises with rising dynamic viscosity.

The monomer solution has, at 20° C., a density of preferably from 1 to 1.3 g/cm$^3$, more preferably from 1.05 to 1.25 g/cm$^3$, most preferably from 1.1 to 1.2 g/cm$^3$.

The monomer solution has, at 20° C., a surface tension of from 0.02 to 0.06 N/m, more preferably from 0.03 to 0.05 N/m, most preferably from 0.035 to 0.045 N/m. The mean droplet diameter in the droplet generation rises with rising surface tension.

Polymerization

The monomer solution is preferably metered into the gas phase to form droplets, i.e. using a system described in WO 2008/069639 A1 and WO 2008/086976 A1. The droplets are generated by means of a droplet plate.

A droplet plate is a plate having a multitude of bores, the liquid entering the bores from the top. The droplet plate or the liquid can be oscillated, which generates a chain of ideally monodisperse droplets at each bore on the underside of the droplet plate. In a preferred embodiment, the droplet plate is not agitated.

The number and size of the bores are selected according to the desired capacity and droplet size. The droplet diameter is typically 1.9 times the diameter of the bore. What is important here is that the liquid to be dropletized does not pass through the bore too rapidly and the pressure drop over the bore is not too great. Otherwise, the liquid is not dropletized, but rather the liquid jet is broken up (sprayed) owing to the high kinetic energy. The Reynolds number based on the throughput per bore and the bore diameter is preferably less than 2000, preferentially less than 1600, more preferably less than 1400 and most preferably less than 1200.

The underside of the droplet plate has at least in part a contact angle preferably of at least 60°, more preferably at least 75° and most preferably at least 90° with regard to water.

The contact angle is a measure of the wetting behavior of a liquid, in particular water, with regard to a surface, and can be determined using conventional methods, for example in accordance with ASTM D 5725. A low contact angle denotes good wetting, and a high contact angle denotes poor wetting.

It is also possible for the droplet plate to consist of a material having a lower contact angle with regard to water, for example a steel having the German construction material code number of 1.4571, and be coated with a material having a larger contact angle with regard to water.

Useful coatings include for example fluorous polymers, such as perfluoroalkoxyethylene, polytetrafluoroethylene, ethylene-chlorotrifluoroethylene copolymers, ethylene-tetrafluoroethylene copolymers and fluorinated polyethylene.

The coatings can be applied to the substrate as a dispersion, in which case the solvent is subsequently evaporated off and the coating is heat treated. For polytetrafluoroethylene this is described for example in U.S. Pat. No. 3,243,321.

Further coating processes are to found under the headword "Thin Films" in the electronic version of "Ullmann's Encyclopedia of Industrial Chemistry" (Updated Sixth Edition, 2000 Electronic Release).

The coatings can further be incorporated in a nickel layer in the course of a chemical nickelization.

It is the poor wettability of the droplet plate that leads to the production of monodisperse droplets of narrow droplet size distribution.

The droplet plate has preferably at least 5, more preferably at least 25, most preferably at least 50 and preferably up to 750, more preferably up to 500 bores, most preferably up to 250. The diameter of the bores is adjusted to the desired droplet size.

The separation of the bores is usually from 10 to 50 mm, preferably from 12 to 40 mm, more preferably from 14 to 35 mm, most preferably from 15 to 30 mm. Smaller separations of the bores cause agglomeration of the polymerizing droplets.

The diameter of the bores is preferably from 50 to 500 μm, more preferably from 100 to 300 μm, most preferably from 150 to 250 μm.

The temperature of the monomer solution as it passes through the bore is preferably from 5 to 80° C., more preferably from 10 to 70° C., most preferably from 30 to 60° C.

A gas flows through the reaction chamber. The carrier gas is conducted through the reaction chamber in cocurrent to the free-falling droplets of the monomer solution, i.e. from the top downward. After one pass, the gas is preferably recycled at least partly, preferably to an extent of at least 50%, more preferably to an extent of at least 75%, into the reaction chamber as cycle gas. Typically, a portion of the carrier gas is discharged after each pass, preferably up to 10%, more preferably up to 3% and most preferably up to 1%.

The oxygen content of the carrier gas is preferably from 0.5 to 15% by volume, more preferably from 1 to 10% by volume, most preferably from 2 to 7% by weight.

As well as oxygen, the carrier gas preferably comprises nitrogen. The nitrogen content of the gas is preferably at least 80% by volume, more preferably at least 90% by volume, most preferably at least 95% by volume. Other possible carrier gases may be selected from carbondioxide, argon, xenon, krypton, neon, helium. Any mixture of carrier gases may be used. The carrier gas may also become loaded with water and/or acrylic acid vapors.

The gas velocity is preferably adjusted such that the flow in the reaction chamber is directed, for example no convection currents opposed to the general flow direction are present, and is from 0.1 to 2.5 m/s, preferably from 0.3 to 1.5 m/s, more preferably from 0.5 to 1.2 m/s, even more preferably from 0.6 to 1.0 m/s, most preferably from 0.7 to 0.9 m/s.

The gas entrance temperature is controlled in such a way that the gas exit temperature, i.e. the temperature with which the gas leaves the reaction chamber, is from 90 to 150° C., preferably from 100 to 140° C., more preferably from 105 to 135° C., even more preferably from 110 to 130° C., most preferably from 115 to 125° C.

The water-absorbent polymer particles can be divided into three categories: water-absorbent polymer particles of Type 1 are particles with one cavity, water-absorbent polymer particles of Type 2 are particles with more than one cavity, and water-absorbent polymer particles of Type 3 are solid particles with no visible cavity.

The morphology of the water-absorbent polymer particles can be controlled by the reaction conditions during polymerization. Water-absorbent polymer particles having a high amount of particles with one cavity (Type 1) can be prepared by using low gas velocities and high gas exit temperatures. Water-absorbent polymer particles having a high amount of particles with more than one cavity (Type 2) can be prepared by using high gas velocities and low gas exit temperatures.

Water-absorbent polymer particles having more than one cavity (Type 2) show an improved mechanical stability.

The reaction can be carried out under elevated pressure or under reduced pressure; preference is given to a reduced pressure of up to 100 mbar relative to ambient pressure.

The reaction off-gas, i.e. the gas leaving the reaction chamber, may, for example, be cooled in a heat exchanger. This condenses water and unconverted monomer a). The reaction off-gas can then be reheated at least partly and recycled into the reaction chamber as cycle gas. A portion of the reaction off-gas can be discharged and replaced by fresh gas, in which case water and unconverted monomers a) present in the reaction off-gas can be removed and recycled.

Particular preference is given to a thermally integrated system, i.e. a portion of the waste heat in the cooling of the off-gas is used to heat the cycle gas.

The reactors can be trace-heated. In this case, the trace heating is adjusted such that the wall temperature is at least 5° C. above the internal reactor temperature and condensation on the reactor walls is reliably prevented.

Thermal Posttreatment

The residual monomers in the water-absorbent polymer particles obtained by dropletization polymerization can be removed by a thermal posttreatment in the presence of a gas stream. The residual monomers can be removed better at relatively high temperatures and relatively long residence times. What is important here is that the water-absorbent polymer particles are not too dry. In the case of excessively dry particles, the residual monomers decrease only insignificantly. Too high a water content increases the caking tendency of the water-absorbent polymer particles. In order that the water-absorbent polymer particles do not dry too rapidly during the thermal posttreatment, the gas flowing in shall already comprise steam.

The thermal posttreatment can be done in an internal and/or an external fluidized bed. An internal fluidized bed means that the product of the dropletization polymerization is accumulated in a fluidized bed at the bottom of the reaction chamber.

In the fluidized state, the kinetic energy of the polymer particles is greater than the cohesion or adhesion potential between the polymer particles.

The fluidized state can be achieved by a fluidized bed. In this bed, there is upward flow toward the water-absorbing polymer particles, so that the particles form a fluidized bed. The height of the fluidized bed is adjusted by gas rate and gas velocity, i.e. via the pressure drop of the fluidized bed (kinetic energy of the gas).

The velocity of the gas stream in the fluidized bed is preferably from 0.5 to 2.5 m/s, more preferably from 0.6 to 1.5 m/s, most preferably from 0.7 to 1.0 m/s.

In a more preferred embodiment of the present invention the thermal posttreatment is done in an external mixer with moving mixing tools, preferably horizontal mixers, such as screw mixers, disk mixers, screw belt mixers and paddle mixers. Suitable mixers are, for example, Becker shovel mixers (Gebr. Lödige Maschinenbau GmbH; Paderborn; Germany), Nara paddle mixers (NARA Machinery Europe; Frechen; Germany), Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; U.S.A.) and Ruberg continuous flow mixers (Gebrüder Ruberg GmbH & Co KG, Nieheim, Germany). Ruberg continuous flow mixers, Becker shovel mixers and Pflugschar® plowshare mixers are preferred.

The moisture content of the water-absorbent polymer particles during the thermal posttreatment is preferably from 3 to 50% by weight, more preferably from 6 to 30% by weight, most preferably from 8 to 20% by weight.

The temperature of the water-absorbent polymer particles during the thermal posttreatment is preferably from 60 to 140° C., more preferably from 70 to 125° C., very particularly from 80 to 110° C.

The average residence time in the mixer used for the thermal posttreatment is preferably from 10 to 120 minutes, more preferably from 15 to 90 minutes, most preferably from 20 to 60 minutes.

The steam content of the gas is preferably from 0.01 to 1 kg per kg of dry gas, more preferably from 0.05 to 0.5 kg per kg of dry gas, most preferably from 0.1 to 0.25 kg per kg of dry gas.

The thermal posttreatment can be done in a discontinuous external mixer or a continuous external mixer.

The amount of gas to be used in the discontinuous external mixer is preferably from 0.01 to 5 $Nm^3/h$, more preferably from 0.05 to 2 $Nm^3/h$, most preferably from 0.1 to 0.5 $Nm^3/h$, based in each case on kg water-absorbent polymer particles.

The amount of gas to be used in the continuous external mixer is preferably from 0.01 to 5 $Nm^3/h$, more preferably from 0.05 to 2 $Nm^3/h$, most preferably from 0.1 to 0.5 $Nm^3/h$, based in each case on kg/h throughput of water-absorbent polymer particles.

The other constituents of the gas are preferably nitrogen, carbondioxide, argon, xenon, krypton, neon, helium, air or air/nitrogen mixtures, more preferably nitrogen or air/nitrogen mixtures comprising less than 10% by volume of oxygen. Oxygen may cause discoloration.

Postcrosslinking

The water-absorbent polymer particles are preferably postcrosslinked for further improvement of the properties.

Postcrosslinkers are compounds which comprise groups which can form at least two covalent bonds with the carboxylate groups of the polymer particles. Suitable compounds are, for example, polyfunctional amines, polyfunctional amidoamines, polyfunctional epoxides, as described in EP 0 083 022 A2, EP 0 543 303 A1 and EP 0 937 736 A2, di- or polyfunctional alcohols as described in DE 33 14 019 A1, DE 35 23 617 A1 and EP 0 450 922 A2, or β-hydroxyalkylamides, as described in DE 102 04 938 A1 and U.S. Pat. No. 6,239,230.

Polyvinylamine, polyamidoamines and polyvinylalcohole are examples of multifunctional polymeric postcrosslinkers.

In addition, DE 40 20 780 C1 describes cyclic carbonates, DE 198 07 502 A1 describes 2-oxazolidone and its derivatives such as 2-hydroxyethyl-2-oxazolidone, DE 198 07 992 C1 describes bis- and poly-2-oxazolidinones, DE 198 54 573 A1 describes 2-oxotetrahydro-1,3-oxazine and its derivatives, DE 198 54 574 A1 describes N-acyl-2-oxazolidones, DE 102 04 937 A1 describes cyclic ureas, DE 103 34 584 A1 describes bicyclic amide acetals, EP 1 199 327 A2 describes oxetanes and cyclic ureas, and WO 2003/31482 A1 describes morpholine-2,3-dione and its derivatives, as suitable postcrosslinkers.

Particularly preferred postcrosslinkers are ethylene carbonate, mixtures of propylene glycol and 1,4-butanediol, 1,3-propandiole, mixtures of 1,3-propandiole and 1,4-butanediole, ethylene glycol diglycidyl ether and reaction products of polyamides and epichlorohydrin.

Very particularly preferred postcrosslinkers are 2-hydroxyethyl-2-oxazolidone, 2-oxazolidone and 1,3-propanediol.

In addition, it is also possible to use postcrosslinkers which comprise additional polymerizable ethylenically unsaturated groups, as described in DE 37 13 601 A1.

The amount of postcrosslinker is preferably from 0.001 to 2% by weight, more preferably from 0.02 to 1% by weight, most preferably from 0.05 to 0.2% by weight, based in each case on the polymer.

Polyvalent cations are preferably applied to the particle surface in addition to the postcrosslinkers before, during or after the postcrosslinking.

The polyvalent cations are, for example, divalent cations such as the cations of zinc, magnesium, calcium, iron and strontium, trivalent cations such as the cations of aluminum, iron, chromium, rare earths and manganese, tetravalent cations such as the cations of titanium and zirconium, and also mixtures thereof. Possible counterions are chloride, bromide, sulfate, hydrogensulfate, carbonate, hydrogencarbonate, nitrate, hydroxide, phosphate, hydrogenphosphate, dihydrogenphosphate and carboxylate, such as acetate, glycolate, tartrate, formiate, propionate, and lactate, and also mixtures thereof. Aluminum sulfate, aluminum acetate, and aluminum lactate are preferred. Apart from metal salts, it is also possible to use polyamines and/or polymeric amines as polyvalent cations. A single metal salt can be used as well as any mixture of the metal salts and/or the polyamines above.

The amount of polyvalent cation used is, for example, from 0.001 to 1.5% by weight, preferably from 0.005 to 1% by weight, more preferably from 0.02 to 0.8% by weight, based in each case on the polymer.

The postcrosslinking is typically performed in such a way that a solution of the postcrosslinker is sprayed onto the hydrogel or the dry polymer particles. After the spraying, the polymer particles coated with the postcrosslinker are dried thermally and cooled, and the postcrosslinking reaction can take place either before or during the drying.

The spraying of a solution of the postcrosslinker is preferably performed in mixers with moving mixing tools, such as screw mixers, disk mixers and paddle mixers. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Ruberg continuous flow mixers and horizontal Pflugschar® plowshare mixers are preferred. The postcrosslinker solution can also be sprayed into a fluidized bed.

If an external mixer or an external fluidized bed is used for thermal posttreatment, the solution of the postcrosslinker can also be sprayed into the external mixer or the external fluidized bed.

The postcrosslinkers are typically used as an aqueous solution. The addition of nonaqueous solvent can be used to adjust the penetration depth of the postcrosslinker into the polymer particles.

The thermal drying is preferably carried out in contact dryers, more preferably paddle dryers, most preferably disk dryers. Suitable driers are, for example, Hosokawa Bepex® horizontal paddle driers (Hosokawa Micron GmbH; Leingarten; Geimany), Hosokawa Bepex® disk driers (Hosokawa Micron GmbH; Leingarten; Germany), Holo-Flite® dryers (Metso Minerals Industries Inc.; Danville; U.S.A.) and Nara paddle driers (NARA Machinery Europe; Frechen; Germany). Nara paddle driers and, in the case of using polyfunctional epoxides, Holo-Flite® dryers are preferred. Moreover, it is also possible to use fluidized bed dryers.

The drying can be effected in the mixer itself, by heating the jacket or blowing in warm air. Equally suitable is a downstream dryer, for example a shelf dryer, a rotary tube oven or a heatable screw. It is particularly advantageous to mix and dry in a fluidized bed dryer.

Preferred drying temperatures are in the range from 50 to 220° C., preferably from 100 to 180° C., more preferably from 120 to 160° C., most preferably from 130 to 150° C. The preferred residence time at this temperature in the reaction mixer or dryer is preferably at least 10 minutes, more preferably at least 20 minutes, most preferably at least 30 minutes, and typically at most 60 minutes.

It is preferable to cool the polymer particles after thermal drying. The cooling is preferably carried out in contact coolers, more preferably paddle coolers, most preferably disk coolers. Suitable coolers are, for example, Hosokawa Bepex® horizontal paddle coolers (Hosokawa Micron GmbH; Leingarten; Germany), Hosokawa Bepex® disk coolers (Hosokawa Micron GmbH; Leingarten; Germany), Holo-Flite® coolers (Metso Minerals Industries Inc.; Danville; U.S.A.) and Nara paddle coolers (NARA Machinery Europe; Frechen; Germany). Moreover, it is also possible to use fluidized bed coolers.

In the cooler the polymer particles are cooled to temperatures of in the range from 20 to 150° C., preferably from 40 to 120° C., more preferably from 60 to 100° C., most preferably from 70 to 90° C. Cooling using warm water is preferred, especially when contact coolers are used.

Coating

To improve the properties, the water-absorbent polymer particles can be coated and/or optionally moistened. The internal fluidized bed, the external fluidized bed and/or the external mixer used for the thermal posttreatment and/or a separate coater (mixer) can be used for coating of the water-absorbent polymer particles. Further, the cooler and/or a separate coater (mixer) can be used for coating/moistening of the postcrosslinked water-absorbent polymer particles. Suitable coatings for controlling the acquisition behavior and improving the permeability (SFC or GBP) are, for example, inorganic inert substances, such as water-insoluble metal salts, organic polymers, cationic polymers and polyvalent metal cations. Suitable coatings for improving the color stability are, for example reducing agents and anti-oxidants. Suitable coatings for dust binding are, for example, polyols. Suitable coatings against the undesired caking tendency of the polymer particles are, for example, fumed silica, such as Aerosil® 200, and surfactants, such as Span® 20. Preferred coatings are aluminium monoacetate, aluminium sulfate, aluminium lactate, Brüggolite® FF7 and Span® 20.

Suitable inorganic inert substances are silicates such as montmorillonite, kaolinite and talc, zeolites, activated carbons, polysilicic acids, magnesium carbonate, calcium carbonate, calcium phosphate, barium sulfate, aluminum oxide, titanium dioxide and iron(II) oxide. Preference is given to using polysilicic acids, which are divided between precipitated silicas and fumed silicas according to their mode of preparation. The two variants are commercially available under the names Silica FK, Sipernat®, Wessalon® (precipitated silicas) and Aerosil® (fumed silicas) respectively. The inorganic inert substances may be used as dispersion in an aqueous or water-miscible dispersant or in substance.

When the water-absorbent polymer particles are coated with inorganic inert substances, the amount of inorganic inert substances used, based on the water-absorbent polymer particles, is preferably from 0.05 to 5% by weight, more preferably from 0.1 to 1.5% by weight, most preferably from 0.3 to 1% by weight.

Suitable organic polymers are polyalkyl methacrylates or thermoplastics such as polyvinyl chloride, waxes based on polyethylene or polypropylene or polyamides or polytetrafluoro-ethylene. Other examples are: styrene-isoprene-styrene block-copolymers or styrene-butadiene-styrene block-copolymers.

Suitable cationic polymers are polyalkylenepolyamines, cationic derivatives of polyacrylamides, polyethyleneimines and polyquaternary amines.

Polyquaternary amines are, for example, condensation products of hexamethylenediamine, dimethylamine and epichlorohydrin, condensation products of dimethylamine and epichlorohydrin, copolymers of hydroxyethylcellulose and diallyldimethylammonium chloride, copolymers of acrylamide and α-methacryloyloxyethyltrimethylammonium chloride, condensation products of hydroxyethylcellulose, epichlorohydrin and trimethylamine, homopolymers of diallyldimethylammonium chloride and addition products of epichlorohydrin to amidoamines. In addition, polyquaternary amines can be obtained by reacting dimethyl sulfate with polymers such as polyethyleneimines, copolymers of vinylpyrrolidone and dimethylaminoethyl methacrylate or copolymers of ethyl methacrylate and diethylaminoethyl methacrylate. The polyquaternary amines are available within a wide molecular weight range.

However, it is also possible to generate the cationic polymers on the particle surface, either through reagents which can form a network with themselves, such as addition products of epichlorohydrin to polyamidoamines, or through the application of cationic polymers which can react with an added crosslinker, such as polyamines or polyimines in combination with polyepoxides, polyfunctional esters, polyfunctional acids or polyfunctional (meth)acrylates.

It is possible to use all polyfunctional amines having primary or secondary amino groups, such as polyethyleneimine, polyallylamine and polylysine. The liquid sprayed preferably comprises at least one polyamine, for example polyvinylamine or a partially hydrolysed polyvinylformamide.

The cationic polymers may be used as a solution in an aqueous or water-miscible solvent, as dispersion in an aqueous or water-miscible dispersant or in substance.

When the water-absorbent polymer particles are coated with a cationic polymer, the use amount of cationic polymer based on the water-absorbent polymer particles is usually not less than 0.001% by weight, typically not less than 0.01% by weight, preferably from 0.1 to 15% by weight, more preferably from 0.5 to 10% by weight, most preferably from 1 to 5% by weight.

Suitable polyvalent metal cations are $Mg^{2+}$, $Ca^{2+}$, $Al^{3+}$, $Sc^{3+}$, $Ti^{4+}$, $Mn^{2+}$, $Fe^{2+/3o}$, $Co^{2+}$, $Ni^{2+}$, $Cu^{+/2+}$, $Zn^{2+}$, $Y^{3+}$, $Zr^{4+}$, $Ag^+$, $La^{3+}$, $Ce^{4+}$, $Hf^{4+}$ and $Au^{+/3+}$; preferred metal cations are $Mg^{2+}$, $Ca^{2+}$, $Al^{3+}$, $Ti^{4+}$, $Zr^{4+}$ and $La^{3+}$; particularly preferred metal cations are $Al^{3+}$, $Ti^{4+}$ and $Zr^{4+}$. The metal cations may be used either alone or in a mixture with one another. Suitable metal salts of the metal cations mentioned are all of those which have a sufficient solubility in the solvent to be used. Particularly suitable metal salts have weakly complexing anions, such as chloride hydroxide, carbonate nitrate and sulfate. The metal salts are preferably used as a solution or as a stable aqueous colloidal dispersion. The solvents used for the metal salts may be water, alcohols, dimethylformamide, dimethyl sulfoxide and mixtures thereof Particular preference is given to water and water/alcohol mixtures, such as water/methanol, water/isopropanol, water/1,3-propanediole, water/1,2-propandiole/1,4-butanediole or water/propylene glycol.

When the water-absorbent polymer particles are coated with a polyvalent metal cation, the amount of polyvalent metal cation used, based on the water-absorbent polymer particles, is preferably from 0.05 to 5% by weight, more preferably from 0.1 to 1.5% by weight, most preferably from 0.3 to 1% by weight.

Suitable reducing agents are, for example, sodium sulfite, sodium hydrogensulfite (sodium bisulfite), sodium dithionite, sulfinic acids and salts thereof, ascorbic acid, sodium hypophosphite, sodium phosphite, and phosphinic acids and salts thereof. Preference is given, however, to salts of hypophosphorous acid, for example sodium hypophosphite, salts of sulfinic acids, for example the disodium salt of 2-hydroxy-2-sulfinatoacetic acid, and addition products of aldehydes, for example the disodium salt of 2-hydroxy-2-sulfonatoacetic acid. The reducing agent used can be, however, a mixture of the sodium salt of 2-hydroxy-2-sulfinatoacetic acid, the disodium salt of 2-hydroxy-2-sulfonatoacetic acid and sodium bisulfite. Such mixtures are obtainable as Brüggolite® FF6 and Brüggolite® FF7 (Brüggemann Chemicals; Heilbronn; Germany).

The reducing agents are typically used in the form of a solution in a suitable solvent, preferably water. The reducing agent may be used as a pure substance or any mixture of the above reducing agents may be used When the water-absorbent polymer particles are coated with a reducing agent, the amount of reducing agent used, based on the water-absorbent polymer particles, is preferably from 0.01 to 5% by weight, more preferably from 0.05 to 2% by weight, most preferably from 0.1 to 1% by weight.

Suitable polyols are polyethylene glycols having a molecular weight of from 400 to 20000 g/mol, polyglycerol, 3- to 100-tuply ethoxylated polyols, such as trimethylolpropane, glycerol, sorbitol and neopentyl glycol. Particularly suitable polyols are 7- to 20-tuply ethoxylated glycerol or trimethylolpropane, for example Polyol TP 70® (Perstorp AB, Perstorp, Sweden). The latter have the advantage in particular that they lower the surface tension of an aqueous extract of the water-absorbent polymer particles only insignificantly. The polyols are preferably used as a solution in aqueous or water-miscible solvents.

When the water-absorbent polymer particles are coated with a polyol, the use amount of polyol, based on the water-absorbent polymer particles, is preferably from 0.005 to 2% by weight, more preferably from 0.01 to 1% by weight, most preferably from 0.05 to 0.5% by weight.

The coating is preferably performed in mixers with moving mixing tools, such as screw mixers, disk mixers, paddle mixers and drum coater. Suitable mixers are, for example, horizontal Pflugschar® plowshare mixers (Gebr. Lödige Maschinenbau GmbH; Paderborn; Germany), Vrieco-Nauta Continuous Mixers (Hosokawa Micron BV; Doetinchem; the Netherlands), Processall Mixmill Mixers (Processall Incorporated; Cincinnati; US) and Ruberg continuous flow mixers (Gebrüder Ruberg GmbH & Co KG, Nieheim, Germany). Moreover, it is also possible to use a fluidized bed for mixing.

Agglomeration

The water-absorbent polymer particles can further selectively be agglomerated. The agglomeration can take place after the polymerization, the thermal posttreatment, the postcrosslinking or the coating.

Useful agglomeration assistants include water and water-miscible organic solvents, such as alcohols, tetrahydrofuran and acetone; water-soluble polymers can be used in addition.

For agglomeration a solution comprising the agglomeration assistant is sprayed onto the water-absorbing polymeric particles. The spraying with the solution can, for example, be carried out in mixers having moving mixing implements, such as screw mixers, paddle mixers, disk mixers, plowshare mixers and shovel mixers. Useful mixers include for example Lödige® mixers, Bepex® mixers, Nauta® mixers, Processall® mixers and Schugi® mixers. Vertical mixers are preferred. Fluidized bed apparatuses are particularly preferred.

Combination of Thermal Posttreatment, Postcrosslinking and Optionally Coating

In a preferred embodiment of the present invention the steps of thermal posttreatment and postcrosslinking are combined in one process step. Such combination allows the use of very reactive postcrosslinkers without having any risk of any residual postcrosslinker in the finished product. It also allows the use of low cost equipment and moreover the process can be run at low temperatures which is cost-efficient and avoids discoloration and loss of performance properties of the finished product by thermal degradation.

Postcrosslinkers in this particular preferred embodiment are selected from epoxides, aziridines, polyfuntional epoxides, and polyfunctional aziridines. Examples are ethylene glycol diglycidyl ether, propylene glycol diglycidyl ether, polyethylene glycol diglycidyl ether, polyglycerol polyglycidyl ether, glycerol polyglycidyl ether, sorbitol polyglycidyl ether, pentaerythritol polyglycidyl ether. Such compounds are available for example under the trade name Denacol® (Nagase ChemteX Corporation, Osaka, Japan). These compounds react with the carboxylate groups of the water-absorbent polymers to form crosslinks already at product temperatures of less than 160° C.

The mixer may be selected from any of the equipment options cited in the thermal posttreatment section. Ruberg continuous flow mixers, Becker shovel mixers and Pflugschar® plowshare mixers are preferred.

In this particular preferred embodiment the postcrosslinking solution is sprayed onto the water-absorbent polymer particles under agitation. The temperature of the water-absorbent polymer particles inside the mixer is at least 60° C., preferably at least 80° C., more preferably at least 90° C., most preferably at least 100° C., and preferably not more than 160° C., more preferably not more than 140° C., most preferably not more than 115° C. Thermal posttreatment and postcrosslinking are performed in the presence of a gas stream having a moisture content cited in the thermal posttreatment section.

Following the thermal posttreatment/postcrosslinking the water-absorbent polymer particles are dried to the desired moisture level and for this step any dryer cited in the postcrosslinking section may be selected. However, as only drying needs to be accomplished in this particular preferred embodiment it is possible to use simple and low cost heated contact dryers like a heated screw dryer, for example a Holo-Flite® dryer (Metso Minerals Industries Inc.; Danville; U.S.A.). Alternatively a fluidized bed may be used. In cases where the product needs to be dried with a predetermined and narrow residence time it is possible to use torus disc dryers or paddle dryers, for example a Nara paddle dryer (NARA Machinery Europe; Frechen; Germany), but designed for and operated with low pressure steam or heating liquid as the product temperature during drying does not need to exceed 160° C., preferably does not need to exceed 150° C., more preferably does not need to exceed 140° C., most preferably from 90 to 135° C.

In a preferred embodiment of the present invention, polyvalent cations cited in the postcrosslinking section are applied to the particle surface before, during or after addition of the postcrosslinker by using different addition points along the axis of a horizontal mixer.

In a very particular preferred embodiment of the present invention the steps of thermal posttreatment, postcrosslinking, and coating are combined in one process step. Suitable coatings are cationic polymers, surfactants, and inorganic inert substances that are cited in the coating section. The coating agent can be applied to the particle surface before, during or after addition of the postcrosslinker also by using different addition points along the axis of a horizontal mixer.

The polyvalent cations and/or the cationic polymers can act as additional scavengers for residual postcrosslinkers. In a preferred embodiment of the present invention the postcrosslinkers are added prior to the polyvalent cations and/or the cationic polymers to allow the postcrosslinker to react first.

The surfactants and/or the inorganic inert substances can be used to avoid sticking or caking during this process step under humid atmospheric conditions. A preferred surfactant is Span® 20. Preferred inorganic inert substances are precipitated silicas and fumed silcas in form of powder or dispersion.

The amount of total liquid used for preparing the solutions/dispersions is typically from 0.01% to 25% by weight, preferably from 0.5% to 12% by weight, more preferably from 2% to 7% by weight, most preferably from 3% to 6% by weight, in respect to the weight amount of water-absorbent polymer particles to be processed.

Preferred Embodiments are Depicted in FIGS. 1 to 8

FIG. 1: Process scheme (with external fluidized bed)
FIG. 2: Process scheme (without external fluidized bed)
FIG. 3: Arrangement of the T_outlet measurement
FIG. 4: Arrangement of the dropletizer units
FIG. 5: Dropletizer unit (longitudinal cut)
FIG. 6: Dropletizer unit (cross sectional view)
FIG. 7: Process scheme (external thermal posttreatment and postcrosslinking)
FIG. 8: Process scheme (external thermal posttreatment, postcrosslinking and coating)

The reference numerals have the following meanings:
1 Drying gas inlet pipe
2 Drying gas amount measurement
3 Gas distributor
4 Dropletizer units
5 Cocurrent spray dryer, cylindrical part
6 Cone
7 T_outlet measurement
8 Tower offgas pipe
9 Baghouse filter
10 Ventilator
11 Quench nozzles
12 Condenser column, counter current cooling
13 Heat exchanger
14 Pump
15 Pump
16 Water outlet
17 Ventilator
18 Offgas outlet
19 Nitrogen inlet
20 Heat exchanger
21 Ventilator
22 Heat exchanger
23 Steam injection via nozzles
24 Water loading measurement
25 Conditioned internal fluidized bed gas
26 Internal fluidized bed product temperature measurement
27 Internal fluidized bed
28 Product discharge into external fluidized bed, rotary valve
19 External fluidized bed
30 Ventilator
31 External fluidized bed offgas outlet to baghouse filter
32 Rotary valve
33 Sieve
34 End product
35 Filtered air inlet
36 Ventilator
37 Heat exchanger
38 Steam injection via nozzles
39 Water loading measurement
40 Conditioned external fluidized bed gas
41 Static mixer
42 Static mixer
43 Initiator feed
44 Initiator feed
45 Monomer feed
46 Fine particle fraction outlet to rework
47 T_outlet measurement (average temperature out of 3 measurements around tower circumference)
48 Dropletizer unit
49 Monomer premixed with initiator feed
50 Spray dryer tower wall
51 Dropletizer unit outer pipe
52 Dropletizer unit inner pipe
53 Dropletizer cassette
54 Teflon block
55 Valve
56 Monomer premixed with initiator feed inlet pipe connector
57 Droplet plate
58 Counter plate
59 Flow channels for temperature control water
60 Dead volume free flow channel for monomer solution
61 Dropletizer cassette stainless steel block
62 External thermal posttreatment
63 Optional coating feed
64 Postcrosslinker feed
65 Thermal dryer (postcrosslinking)
66 Cooler
67 Optional coating/water feed
68 Coater
69 Coating/water feed The drying gas is feed via a gas distributor (3) at the top of the spray dryer as shown in FIG. 1. The drying gas is partly recycled (drying gas loop) via a baghouse filter (9) and a condenser column (12). The pressure inside the spray dryer is below ambient pressure.

Figure 3:
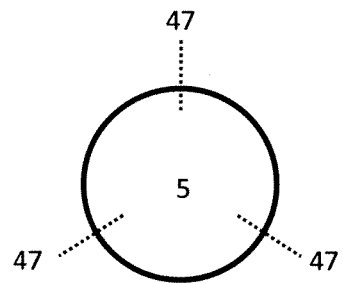
FIG. 3 illustrates an arrangement of the T_outlet measurement.

The spray dryer outlet temperature is preferably measured at three points around the circumference at the end of the cylindrical part as shown in FIG. 3. The single measurements (47) are used to calculate the average cylindrical spray dryer outlet temperature.

The product accumulated in the internal fluidized bed (27). Conditioned internal fluidized bed gas is fed to the internal fluidized bed (27) via line (25). The relative humidity of the internal fluidized bed gas is preferably controlled by adding steam via line (23).

The spray dryer offgas is filtered in baghouse filter (9) and sent to a condenser column (12) for quenching/cooling. After the baghouse filter (9) a recuperation heat exchanger system for preheating the gas after the condenser column (12) can be used. Excess water is pumped out of the condenser column (12) by controlling the (constant) filling level inside the condenser column (12). The water inside the condenser column (12) is cooled by a heat exchanger (13) and pumped countercurrent to the gas via quench nozzles (11) so that the temperature inside the condenser column (12) is preferably from 20 to 100° C., more preferably from 30 to 80° C., most preferably from 40 to 75° C. The water inside the condenser column (12) is set to an alkaline pH by dosing a neutralizing agent to wash out vapors of monomer a). Aqueous solution from the condenser column (12) can be sent back for preparation of the monomer solution.

The condenser column offgas is split to the drying gas inlet pipe (1) and the conditioned internal fluidized bed gas (25). The gas temperatures are controlled via heat exchangers (20) and (22). The hot drying gas is fed to the cocurrent spray dryer via gas distributor (3). The gas distributor (3) consists preferably of a set of plates providing a pressure drop of preferably 1 to 100 mbar, more preferably 2 to 30 mbar, most preferably 4 to 20 mbar, depending on the drying gas amount. Turbulences and/or a centrifugal velocity can also be introduced into the drying gas if desired by using gas nozzles or baffle plates.

The product is discharged from the internal fluidized bed (27) via rotary valve (28) into external fluidized bed (29). Conditioned external fluidized bed gas is fed to the external fluidized bed (29) via line (40). The relative humidity of the external fluidized bed gas is preferably controlled by adding steam via line (38). The product holdup in the internal fluidized bed (27) can be controlled via weir height or rotational speed of the rotary valve (28).

The product is discharged from the external fluidized bed (29) via rotary valve (32) into sieve (33). The product holdup in the external fluidized bed (28) can be controlled via weir height or rotational speed of the rotary valve (32). The sieve (33) is used for sieving off overs/lumps.

The monomer solution is preferably prepared by mixing first monomer a) with a neutralization agent and secondly with crosslinker b). The temperature during neutralization is controlled to preferably from 5 to 60° C., more preferably from 8 to 40° C., most preferably from 10 to 30° C., by using a heat exchanger and pumping in a loop. A filter unit is preferably used in the loop after the pump. The initiators are metered into the monomer solution upstream of the dropletizer by means of static mixers (41) and (42) via lines (43) and (44) as shown in FIG. 1. Preferably a peroxide solution having a temperature of preferably from 5 to 60° C., more preferably from 10 to 50° C., most preferably from 15 to 40° C., is added via line (43) and preferably an azo initiator solution having a temperature of preferably from 2 to 30° C., more preferably from 3 to 15° C., most preferably from 4 to 8° C., is added via line (44). Each initiator is preferably pumped in a loop and dosed via control valves to each dropletizer unit. A second filter unit is preferably used after the static mixer (42). The mean residence time of the monomer solution admixed with the full initiator package in the piping before the droplet plates (57) is preferably less than 60 s, more preferably less than 30 s, most preferably less than 10 s.

Figure 4:
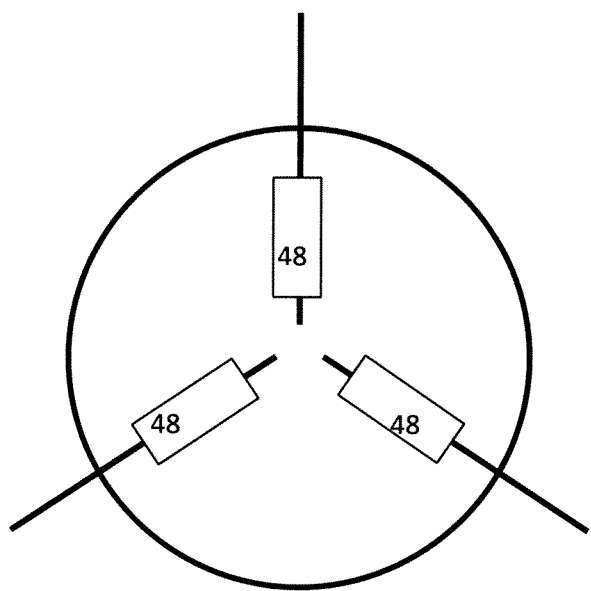
FIG. 4 illustrates an arrangement of the dropletizer units.

For dosing the monomer solution into the top of the spray dryer preferably three dropletizer units are used as shown in FIG. 4.

Figure 5:
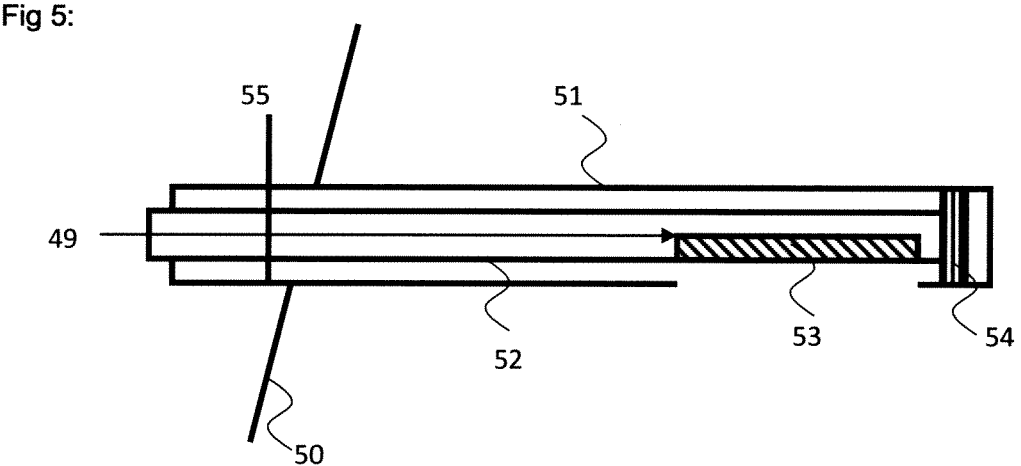
FIG. 5 illustrates a dropletizer unit (longitudinal cut)

A dropletizer unit consists of an outer pipe (51) having an opening for the dropletizer cassette (53) as shown in FIG. 5. The dropletizer cassette (53) is connected with an inner pipe (52). The inner pipe (53) having a PTFE block (54) at the end as sealing can be pushed in and out of the outer pipe (51) during operation of the process for maintenance purposes.

Figure 6:
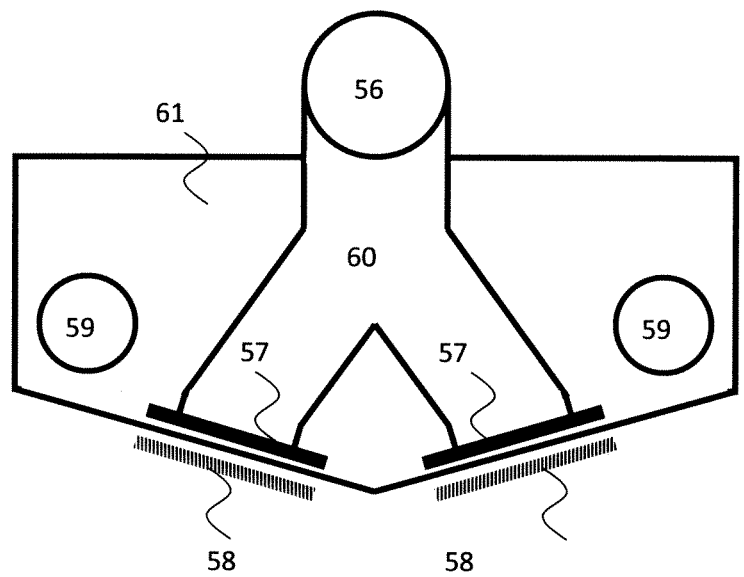
FIG. 6 illustrates a dropletizer unit (cross sectional view)
Figure 7:
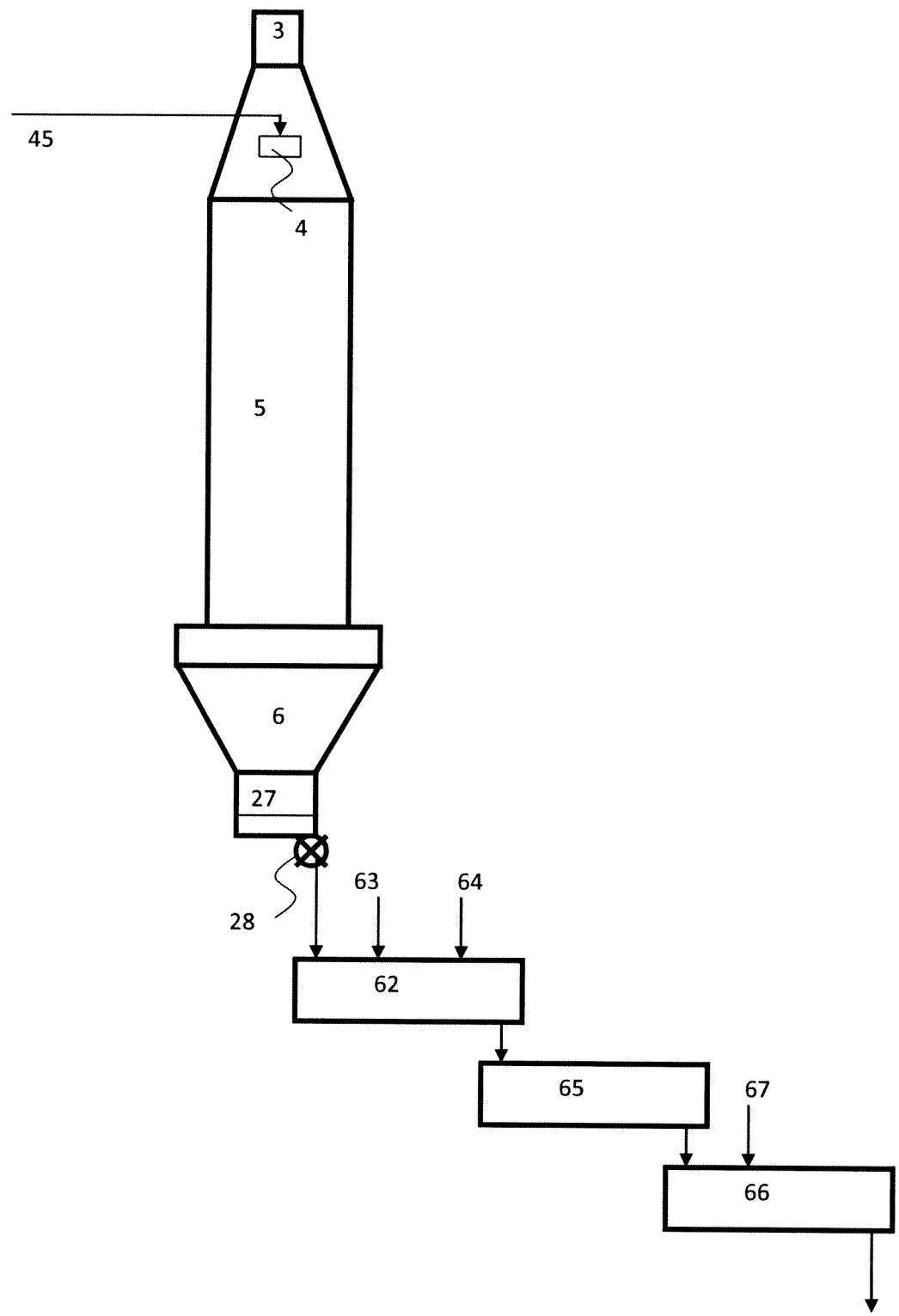
FIG. 7 illustrates a process scheme (external thermal post-treatment and postcrosslinking)

The temperature of the dropletizer cassette (61) is controlled to preferably 5 to 80° C., more preferably 10 to 70° C., most preferably 30 to 60° C., by water in flow channels (59) as shown in FIG. 6.

The dropletizer cassette has preferably from 10 to 1500, more preferably from 50 to 1000, most preferably from 100 to 500, bores having a diameter of preferably from 50 to 500 µm, more preferably from 100 to 300 µm, most preferably from 150 to 250 µm. The bores can be of circular, rectangular, triangular or any other shape. Circular bores are preferred. The ratio of bore length to bore diameter is preferably from 0.5 to 10, more preferably from 0.8 to 5, most preferably from 1 to 3. The droplet plate (57) can have a greater thickness than the bore length when using an inlet bore channel. The droplet plate (57) is preferably long and narrow as disclosed in WO 2008/086976 A1. Multiple rows of bores per droplet plate can be used, preferably from 1 to 20 rows, more preferably from 2 to 5 rows.

The dropletizer cassette (61) consists of a flow channel (60) having essential no stagnant volume for homogeneous distribution of the premixed monomer and initiator solutions and two droplet plates (57). The droplet plates (57) have an angled configuration with an angle of preferably from 1 to 90°, more preferably from 3 to 45°, most preferably from 5 to 20°. Each droplet plate (57) is preferably made of stainless steel or fluorous polymers, such as perfluoroalkoxyethylene, polytetrafluoroethylene, ethylene-chlorotrifluoroethylene copolymers, ethylene-tetrafluoroethylene copolymers and fluorinated polyethylene. Coated droplet plates as disclosed in WO 2007/031441 A1 can also be used. The choice of material for the droplet plate is not limited except that droplet formation must work and it is preferable to use materials which do not catalyze the start of polymerization on its surface.

The throughput of monomer including initiator solutions per dropletizer unit is preferably from 150 to 2500 kg/h, more preferably from 200 to 1000 kg/h, most preferably from 300 to 600 kg/h. The throughput per bore is preferably from 0.5 to 10 kg/h, more preferably from 0.8 to 5 kg/h, most preferably from 1 to 3 kg/h.

Water-Absorbent Polymer Particles

The water-absorbent polymer particles obtainable by dropletization polymerization have a mean sphericity of from 0.86 to 0.99, preferably from 0.86 to 0.99, more preferably from 0.88 to 0.95, most preferably from 0.89 to 0.93. The sphericity (SPHT) is defined as $$SPHT = \frac{4\pi A}{U^2},$$

where A is the cross-sectional area and U is the cross-sectional circumference of the polymer particles. The mean sphericity is the volume-average sphericity.

The mean sphericity can be determined, for example, with the Camsizer® image analysis system (Retsch Technolgy GmbH; Haan; Germany):

For the measurement, the product is introduced through a funnel and conveyed to the falling shaft with a metering channel. While the particles fall past a light wall, they are recorded selectively by a camera. The images recorded are evaluated by the software in accordance with the parameters selected.

To characterize the roundness, the parameters designated as sphericity in the program are employed. The parameters reported are the mean volume-weighted sphericities, the volume of the particles being determined via the equivalent diameter $xc_{min}$. To determine the equivalent diameter $xc_{min}$, the longest chord diameter for a total of 32 different spatial directions is measured in each case. The equivalent diameter $xc_{min}$ is the shortest of these 32 chord diameters. To record the particles, the so-called CCD-zoom camera (CAM-Z) is used. To control the metering channel, a surface coverage fraction in the detection window of the camera (transmission) of 0.5% is predefined.

Water-absorbent polymer particles with relatively low sphericity are obtained by reverse suspension polymerization when the polymer beads are agglomerated during or after the polymerization.

The water-absorbent polymer particles prepared by customary solution polymerization (gel polymerization) are ground and classified after drying to obtain irregular polymer particles. The mean sphericity of these polymer particles is between approx. 0.72 and approx. 0.78.

The water-absorbent polymer particles obtainable by dropletization polymerization have a content of hydrophobic solvent of preferably less than 0.005% by weight, more preferably less than 0.002% by weight and most preferably less than 0.001% by weight. The content of hydrophobic solvent can be determined by gas chromatography, for example by means of the headspace technique.

Water-absorbent polymer particles which have been obtained by reverse suspension polymerization still comprise typically approx. 0.01% by weight of the hydrophobic solvent used as the reaction medium.

The water-absorbent polymer particles obtainable by dropletization polymerization have a dispersant content of typically less than 1% by weight, preferably less than 0.5% by weight, more preferably less than 0.1% by weight and most preferably less than 0.05% by weight.

Water-absorbent polymer particles which have been obtained by reverse suspension polymerization still comprise typically at least 1% by weight of the dispersant, i.e. ethylcellulose, used to stabilize the suspension.

The water-absorbent polymer particles obtainable by dropletization polymerization have a bulk density preferably at least 0.6 g/cm$^3$, more preferably at least 0.65 g/cm$^3$, most preferably at least 0.7 g/cm$^3$, and typically less than 1 g/cm$^3$.

The average particle diameter of the water-absorbent polymer particles obtainable by dropletization polymerization is preferably from 250 to 550 μm, more preferably from 350 to 500 μm, most preferably from 400 to 450 μm.

The particle diameter distribution is preferably less than 0.7, more preferably less than 0.65, more preferably less than 0.6.

Particle morphologies of the water-absorbent polymer particles are investigated in the swollen state by microscope analysis. The water-absorbent polymer particles can be divided into three categories: Type 1 are particles with one cavity having diameters typically from 0.4 to 2.5 mm, Type 2 are particles with more than one cavity having diameters typically from 0.001 to 0.3 mm, and Type 3 are solid particles with no visible cavity. Cavities with less than 1 μm diameter are considered as not visible cavities.

The ratio of particles having one cavity (Type 1) to particles having more than one cavity (Type 2) is preferably less than 1.0, more preferably less than 0.7, most preferably less than 0.4. Lower ratios correlated with higher bulk densities.

The water-absorbent polymer particles obtainable by dropletization polymerization have a moisture content of preferably from 0.5 to 15% by weight, more preferably from 3 to 12% by weight, most preferably from 5 to 10% by weight.

The water-absorbent polymer particles obtainable by dropletization polymerization have a centrifuge retention capacity (CRC) of typically at least 20 g/g, preferably at least 25 g/g, preferentially at least 28 g/g, more preferably at least 30 g/g, most preferably at least 32 g/g. The centrifuge retention capacity (CRC) of the water-absorbent polymer particles is typically less than 60 g/g.

The water-absorbent polymer particles obtainable by dropletization polymerization have an absorbency under a load of 49.2 g/cm$^2$ (AUHL) of typically at least 15 g/g, preferably at least 16 g/g, preferentially at least 20 g/g, more preferably at least 23 g/g, most preferably at least 25 g/g, and typically not more than 50 g/g.

The water-absorbent polymer particles obtainable by dropletization polymerization have a saline flow conductivity (SFC) of typically at least $10\times10^{-7}$ cm$^3$ s/g, usually at least $20\times10^{-7}$ cm$^3$ s/g, preferably at least $50\times10^{-7}$ cm$^3$ s/g, preferentially at least $80\times10^{-7}$ cm$^3$ s/g, more preferably at least $120\times10^{-7}$ cm$^3$ s/g, most preferably at least $150\times10^{-7}$ cm$^3$ s/g, and typically not more than $300\times10^{-7}$ cm$^3$ s/g.

The water-absorbent polymer particles obtainable by dropletization polymerization have a free swell gel bed permeability (GBP) of typically at least 5 Darcies, usually at least 10 Darcies, preferably at least 20 Darcies, preferentially at least 30 Darcies, more preferably at least 40 Darcies, most preferably at least 50 Darcies, and typically not more than 250 Darcies.

The water-absorbent polymer particles obtainable by dropletization polymerization can be mixed with other water-absorbent polymer particles prepared by other processes, i.e. solution polymerization.

C. Fluid-Absorbent Articles

The fluid-absorbent article comprises of
(A) an upper liquid-pervious layer
(B) a lower liquid-impervious layer
(C) a fluid-absorbent core between (A) and (B) comprising an optional core cover, a fluid-storage layer comprising
at least 75% by weight water-absorbent polymer particles and an adhesive;
preferably at least 80% by weight water-absorbent polymer particles and an adhesive;
more preferably at least 83% by weight water-absorbent polymer particles and an adhesive;
most preferably at least 85% by weight water-absorbent polymer particles and an adhesive;
and an optional dusting layer
(D) an optional acquisition-distribution layer between (A) and (C), comprising
at least 80% by weight fibrous material and water-absorbent polymer particles;
preferably at least 85% by weight fibrous material and water-absorbent polymer particles;
more preferably at least 90% by weight fibrous material and water-absorbent polymer particles;
most preferably at least 95% by weight fibrous material and water-absorbent polymer particles;
(E) an optional tissue layer disposed immediately above and/or below (C); and
(F) other optional components.

Fluid-absorbent articles are understood to mean, for example, incontinence pads and incontinence briefs for adults or diapers for babies. Suitable fluid-absorbent articles including fluid-absorbent compositions comprising fibrous materials and optionally water-absorbent polymer particles to form fibrous webs or matrices for the substrates, layers, sheets and/or the fluid-absorbent core.

Suitable fluid-absorbent articles are composed of several layers whose individual elements must show preferably definite functional parameter such as dryness for the upper liquid-pervious layer, vapor permeability without wetting through for the lower liquid-impervious layer, a flexible, vapor permeable and thin fluid-absorbent core, showing fast absorption rates and being able to retain highest quantities of body fluids, and an acquisition-distribution layer between the upper layer and the core, acting as transport and distribution layer of the discharged body fluids. These individual elements are combined such that the resultant fluid-absorbent article meets overall criteria such as flexibility, water vapor breathability, dryness, wearing comfort and protection on the one side, and concerning liquid retention, rewet and prevention of wet through on the other side. The specific combination of these layers provides a fluid-absorbent article delivering both high protection levels as well as high comfort to the consumer.

Liquid-Pervious Layer (A)

The liquid-pervious layer (A) is the layer which is in direct contact with the skin. Thus, the liquid-pervious layer is preferably compliant, soft feeling and non-irritating to the consumer's skin. Generally, the term "liquid-pervious" is understood thus permitting liquids, i.e. body fluids such as urine, menses and/or vaginal fluids to readily penetrate through its thickness. The principle function of the liquid-pervious layer is the acquisition and transport of body fluids from the wearer towards the fluid-absorbent core. Typically liquid-pervious layers are formed from any materials known in the art such as nonwoven material, films or combinations thereof. Suitable liquid-pervious layers (A) consist of customary synthetic or semisynthetic fibers or bicomponent fibers or films of polyester, polyolefins, rayon or natural fibers or any combinations thereof. In the case of nonwoven materials, the fibers should generally be bound by binders such as polyacrylates. Additionally the liquid-pervious layer may contain elastic compositions thus showing elastic characteristics allowing to be stretched in one or two directions.

Suitable synthetic fibers are made from polyvinyl chloride, polyvinyl fluoride, polytetrafluorethylene, polyvinylidene chloride, polyacrylics, polyvinyl acetate, polyethylvinyl acetate, non-soluble or soluble polyvinyl alcohol, polyolefins such as polyethylene, polypropylene, polyamides, polyesters, polyurethanes, polystyrenes and the like.

Examples for films are apertured formed thermoplastic films, apertured plastic films, hydroformed thermoplastic films, reticulated thermoplastic films, porous foams, reticulated foams, and thermoplastic scrims.

Examples of suitable modified or unmodified natural fibers include cotton, bagasse, kemp, flax, silk, wool, wood pulp, chemically modified wood pulp, jute, rayon, ethyl cellulose, and cellulose acetate.

Suitable wood pulp fibers can be obtained by chemical processes such as the Kraft and sulfite processes, as well as from mechanical processes, such as ground wood, refiner mechanical, thermo-mechanical, chemi-mechanical and chemi-thermo-mechanical pulp processes. Further, recycled wood pulp fibers, bleached, unbleached, elementally chlorine free (ECF) or total chlorine free (TCF) wood pulp fibers can be used.

The fibrous material may comprise only natural fibers or synthetic fibers or any combination thereof. Preferred materials are polyester, rayon and blends thereof, polyethylene, and polypropylene.

The fibrous material as a component of the fluid-absorbent compositions may be hydrophilic, hydrophobic or can be a combination of both hydrophilic and hydrophobic fibers. The definition of hydrophilic is given in the section "definitions" in the chapter above. The selection of the ratio hydrophilic/hydrophobic and accordingly the amount of hydrophilic and hydrophobic fibers within fluid-absorbent composition will depend upon fluid handling properties and the amount of water-absorbent polymer particles of the resulting fluid-absorbent composition. Such, the use of hydrophobic fibers is preferred if the fluid-absorbent composition is adjacent to the wearer of the fluid-absorbent article, that is to be used to replace partially or completely the upper liquid-pervious layer, preferably formed from hydrophobic nonwoven materials. Hydrophobic fibers can also be member of the lower breathable, but fluid-impervious layer, acting there as a fluid-impervious barrier.

Examples for hydrophilic fibers are cellulosic fibers, modified cellulosic fibers, rayon, polyester fibers such as polyethylen terephthalate, hydrophilic nylon and the like. Hydrophilic fibers can also be obtained from hydrophobic fibers which are hydrophilized by e.g. surfactant-treating or silica-treating. Thus, hydrophilic thermoplastic fibers derived from polyolefins such as polypropylene, polyamides, polystyrenes or the like by surfactant-treating or silica-treating.

To increase the strength and the integrity of the upper-layer, the fibers should generally show bonding sites, which act as crosslinks between the fibers within the layer.

Technologies for consolidating fibers in a web are mechanical bonding, thermal bonding and chemical bonding. In the process of mechanical bonding the fibers are entangled mechanically, e.g., by water jets (spunlace) to give integrity to the web. Thermal bonding is carried out by means of rising the temperature in the presence of low-melting polymers. Examples for thermal bonding processes are spunbonding, through-air bonding and resin bonding.

Preferred means of increasing the integrity are thermal bonding, spunbonding, resin bonding, through-air bonding and/or spunlace.

In the case of thermal bonding, thermoplastic material is added to the fibers. Upon thermal treatment at least a portion of this thermoplastic material is melting and migrates to intersections of the fibers caused by capillary effects. These intersections solidify to bond sites after cooling and increase the integrity of the fibrous matrix. Moreover, in the case of chemically stiffened cellulosic fibers, melting and migration of the thermoplastic material has the effect of increasing the pore size of the resultant fibrous layer while maintaining its density and basis weight. Upon wetting, the structure and integrity of the layer remains stable. In summary, the addition of thermoplastic material leads to improved fluid permeability of discharged body fluids and thus to improved acquisition properties.

Suitable thermoplastic materials including polyolefins such as polyethylene and polypropylene, polyesters, copolyesters, polyvinyl acetate, polyethylvinyl acetate, polyvinyl chloride, polyvinylidene chloride, polyacrylics, polyamides, copolyamides, polystyrenes, polyurethanes and copolymers of any of the mentioned polymers.

Suitable thermoplastic fibers can be made from a single polymer that is a monocomponent fiber. Alternatively, they can be made from more than one polymer, e.g., bi-component or multicomponent fibers. The term "bicomponent fibers" refers to thermoplastic fibers that comprise a core fiber made from a different fiber material than the shell. Typically, both fiber materials have different melting points, wherein generally the sheath melts at lower temperatures. Bi-component fibers can be concentric or eccentric depending whether the sheath has a thickness that is even or uneven through the cross-sectional area of the bi-component fiber. Advantage is given for eccentric bi-component fibers showing a higher compressive strength at lower fiber thickness. Further bi-component fibers can show the feature "uncrimped" (unbent) or "crimped" (bent), further bi-component fibers can demonstrate differing aspects of surface lubricity.

Examples of bi-component fibers include the following polymer combinations: polyethylene/polypropylene, polyethylvinyl acetate/polypropylene, polyethylene/polyester, polypropylene/polyester, copolyester/polyester and the like.

Suitable thermoplastic materials have a melting point of lower temperatures that will damage the fibers of the layer; but not lower than temperatures, where usually the fluid-absorbent articles are stored. Preferably the melting point is between about 75° C. and 175° C. The typical length of thermoplastic fibers is from about 0.4 to 6 cm, preferably from about 0.5 to 1 cm. The diameter of thermoplastic fibers is defined in terms of either denier (grams per 9000 meters) or dtex (grams per 10 000 meters). Typical thermoplastic fibers have a dtex in the range from about 1.2 to 20, preferably from about 1.4 to 10.

A further mean of increasing the integrity of the fluid-absorbent composition is the spunbonding technology. The nature of the production of fibrous layers by means of spunbonding is based on the direct spinning of polymeric granulates into continuous filaments and subsequently manufacturing the fibrous layer.

Spunbond fabrics are produced by depositing extruded, spun fibers onto a moving belt in a uniform random manner followed by thermal bonding the fibers. The fibers are separated during the web laying process by air jets. Fiber bonds are generated by applying heated rolls or hot needles to partially melt the polymer and fuse the fibers together. Since molecular orientation increases the melting point, fibers that are not highly drawn can be used as thermal binding fibers. Polyethylene or random ethylene/propylene copolymers are used as low melting bonding sites.

Besides spunbonding, the technology of resin bonding also belongs to thermal bonding subjects. Using this technology to generate bonding sites, specific adhesives, based on e.g. epoxy, polyurethane and acrylic are added to the fibrous material and the resulting matrix is thermal treated. Thus the web is bonded with resin and/or thermal plastic resins dispersed within the fibrous material.

As a further thermal bonding technology through-air bonding involves the application of hot air to the surface of the fibrous fabric. The hot air is circulated just above the fibrous fabric, but does not push through the fibrous fabric. Bonding sites are generated by the addition of binders. Suitable binders used in through-air thermal bonding include crystalline binder fibers, bi-component binder fibers, and powders. When using crystalline binder fibers or powders, the binder melts entirely and forms molten droplets throughout the nonwoven's cross-section. Bonding occurs at these points upon cooling. In the case of sheath/core binder fibers, the sheath is the binder and the core is the carrier fiber. Products manufactured using through-air ovens tend to be bulky, open, soft, strong, extensible, breathable and absorbent. Through-air bonding followed by immediate cold calendering results in a thickness between a hot roll calendered product and one that has been though-air bonded without compression. Even after cold calendering, this product is softer, more flexible and more extensible than area-bond hot-calendered material.

Spunlacing ("hydroentanglement") is a further method of increasing the integrity of a web. The formed web of loose fibers (usually air-laid or wet-laid) is first compacted and prewetted to eliminate air pockets. The technology of spunlacing uses multiple rows of fine high-speed jets of water to strike the web on a porous belt or moving perforated or patterned screen so that the fibers knot about one another. The water pressure generally increases from the first to the last injectors. Pressures as high as 150 bar are used to direct the water jets onto the web. This pressure is sufficient for most of the nonwoven fibers, although higher pressures are used in specialized applications.

The spunlace process is a nonwovens manufacturing system that employs jets of water to entangle fibers and thereby provide fabric integrity. Softness, drape, conformability, and relatively high strength are the major characteristics of spunlace nonwoven.

In newest researches benefits are found in some structural features of the resulting liquid-pervious layers. For example, the thickness of the layer is very important and influences together with its x-y dimension the acquisition-distribution behavior of the layer. If there is further some profiled structure integrated, the acquisition-distribution behavior can be directed depending on the three-dimensional structure of the layer. Thus 3D-polyethylene in the function of liquid-pervious layer is preferred.

Thus, suitable liquid-pervious layers (A) are nonwoven layers formed from the fibers above by thermal bonding, spunbonding, resin bonding or through-air bonding. Further suitable liquid-pervious layers are 3D-polyethylene layers and spunlace.

Preferably the 3D-polyethylene layers and spunlace show basis weights from 12 to 22 gsm.

Typically liquid-pervious layers (A) extend partially or wholly across the fluid-absorbent structure and can extend into and/or form part of all the preferred sideflaps, side wrapping elements, wings and ears.

Liquid-Impervious Layer (B)

The liquid-impervious layer (B) prevents the exudates absorbed and retained by the fluid-absorbent core from wetting articles which are in contact with the fluid-absorbent article, as for example bedsheets, pants, pyjamas and undergarments. The liquid-impervious layer (B) may thus comprise a woven or a nonwoven material, polymeric films such as thermoplastic film of polyethylene or polypropylene, or composite materials such as film-coated nonwoven material.

Suitable liquid-impervious layers include nonwoven, plastics and/or laminates of plastic and nonwoven. Both, the plastics and/or laminates of plastic and nonwoven may appropriately be breathable, that is, the liquid-impervious layer (B) can permit vapors to escape from the fluid-absorbent material. Thus the liquid-impervious layer has to have a definite water vapor transmission rate and at the same time the level of impermeability. To combine these features, suitable liquid-impervious layers including at least two layers, e.g. laminates from fibrous nonwoven having a specified basis weight and pore size, and a continuous three-dimensional film of e.g. polyvinylalcohol as the second layer having a specified thickness and optionally having pore structure. Such laminates acting as a barrier and showing no liquid transport or wet through. Thus, suitable liquid-impervious layers comprising at least a first breathable layer of a porous web which is a fibrous nonwoven, e.g. a composite web of a meltblown nonwoven layer or of a spunbonded nonwoven layer made from synthetic fibers and at least a second layer of a resilient three dimensional web consisting of a liquid-impervious polymeric film, e.g. plastics optionally having pores acting as capillaries, which are preferably not perpendicular to the plane of the film but are disposed at an angle of less than 90° relative to the plane of the film.

Suitable liquid-impervious layers are permeable for vapor. Preferably the liquid-impervious layer is constructed from vapor permeable material showing a water vapor transmission rate (WVTR) of at least about 100 gsm per 24 hours, preferably at least about 250 gsm per 24 hours and most preferred at least about 500 gsm per 24 hours.

Preferably the liquid-impervious layer (B) is made of nonwoven comprising hydrophobic materials, e.g. synthetic fibers or a liquid-impervious polymeric film comprising plastics e.g. polyethylene. The thickness of the liquid-impervious layer is preferably 15 to 30 μm.

Further, the liquid-impervious layer (B) is preferably made of a laminate of nonwoven and plastics comprising a nonwoven having a density of 12 to 15 gsm and a polyethylene layer having a thickness of about 10 to 20 μm.

The typically liquid-impervious layer (B) extends partially or wholly across the fluid-absorbent structure and can extend into and/or form part of all the preferred sideflaps, side wrapping elements, wings and ears.

Fluid-Absorbent Core (C)

The fluid-absorbent core (C) is disposed between the upper liquid-pervious layer (A) and the lower liquid-impervious layer (B). Suitable fluid-absorbent cores (C) may be selected from any of the fluid-absorbent core-systems known in the art provided that requirements such as vapor permeability, flexibility and thickness are met. Suitable fluid-absorbent cores refer to any fluid-absorbent composition whose primary function is to acquire, transport, distribute, absorb, store and retain discharged body fluids.

Figure 11:
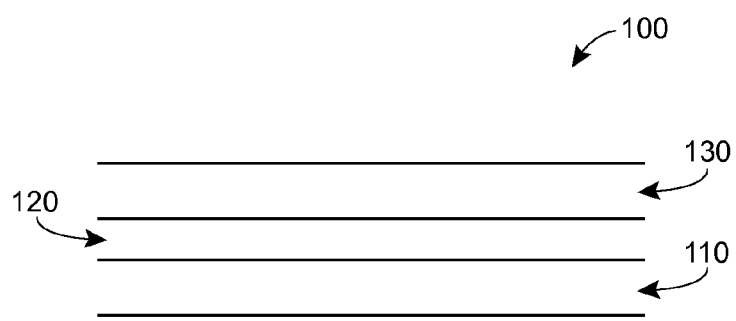
FIG. 11 shows a side view of an absorbent core.

FIG. 11 illustrates one embodiment of an absorbent core of the present invention. In particular, FIG. 11 shows absorbent core 100 having a substrate layer 110, an adhesive layer 120, and a water-absorbent polymer particle layer 130.

The top view area of the fluid-absorbent core (C) is preferably at least 200 cm$^2$, more preferably at least 250 cm$^2$, most preferably at least 300 cm$^2$. The top view area is the part of the core that is face-to-face to the upper liquid-pervious layer.

The fluid-absorbent core comprises a substrate layer, i.e. a nonwoven layer or a tissue paper, water-absorbent polymer particles, and an adhesive.

Suitable nonwoven layers for the present invention include those made using synthetic polymeric fibers. The synthetic polymeric fibers may be formed from any polymeric material capable of forming fibers which fibers can be formed into a nonwoven layer. Suitable polymeric material from which the synthetic polymeric fibers may be formed include polyolefins, such as polyethylene, polypropylene, and the like, polyesters such as polyethylene terephthalate and the like, polyamides such as nylon 6, nylon 6,6, poly(iminocarboxylpentamethylene) and the like, acrylics, and modified cellulosic material, such as cellulose acetate and rayon; as well as mixtures and copolymers thereof.

The synthetic polymeric fibers may be formed by meltblowing, through a spunbond process, by extrusion and drawing, or other wet, dry and melt spinning methods known to those skilled in the art. The synthetic polymeric fibers from which the nonwoven layer is formed may have a discrete length or may be substantially continuous. For example, if the synthetic polymeric fibers are formed by meltblowing, the fibers may be substantially continuous (few visible ends). If the fibers are formed by extrusion and drawing to produce a tow, the tow may be used as produced or cut into staple fibers having a length, for example, of from about 25 to 75 mm or short cut into lengths of from about 1 to 25 mm. The synthetic polymeric fibers may suitably have a maximum cross-sectional dimension of from about 0.5 to 50 μm as determined by microscopic measurement using an optical microscope and a calibrated stage micrometer or by measurement from Scanning Electron photomicrographs.

The nonwoven layers may be formed directly through a spunbond or meltblown process, or by carding or air-laying staple or short cut fibers. Other methods of forming nonwoven layers known to those skilled in the art may be suited for use in the present invention. The nonwoven layer may subsequently be bonded to enhance structural integrity. Methods of bonding nonwoven layers are known to those skilled in the art and include thermal bonding, point bonding, powder bonding, ultrasonic bonding, chemical bonding, mechanical entanglement, and the like. The fibers may be homogenous fibers or may be a core/sheath or side-by-side fibers known to those skilled in the art as bicomponent fibers.

The nonwoven layer may be formed from a single type of synthetic polymeric fiber or may contain synthetic polymeric fibers formed from different polymeric materials, having different fiber lengths or maximum cross-sectional dimensions. For example, the nonwoven layer may comprise a mixture of (1) bicomponent fibers having a polyethylene sheath and a polypropylene core which bicomponent fibers have a maximum cross-sectional dimension of about 20 μm and a length of about 38 mm and (2) polyester fibers, i.e. polyethylene terephthalate, having a maximum cross-sectional dimension of about 25 μm and a length of about 38 mm. Fibers 1 and 2 may be combined in a weight ratio of from 1:99 to 99:1. The fibers may be uniformly mixed or may be concentrated at opposite planar surfaces of the nonwoven layer.

The nonwoven layer suitably comprises preferably from about 20 to 100% by weight, more preferably from about 25 to 100% by weight, most preferably from about 50 to 100% by weight, synthetic polymeric fibers. In addition to the synthetic polymeric fibers, the nonwoven layer may contain from about 90 to 0% by weight of a non-synthetic polymeric fiber such as wood pulp fluff cotton linters, cotton, and the like.

In one preferred embodiment, the nonwoven layer contains synthetic polymeric fibers which are formed from a polymeric material having a high wet modulus. The importance of the modulus of a material is discussed in the monograph "Absorbency", P. K. Chatterjee, Elsevier, 1985. A polymeric material will be considered to have a high wet modulus when it has a wet modulus greater than about 80% of its dry modulus as determined by the ASTM test method D 2101-91 using modified gauge lengths. It is often desired to form the synthetic polymeric fibers of the nonwoven layer from a polymeric material having a high wet modulus because such materials generally form nonwoven layers which possess a relatively high degree of wet resiliency. The wet resilience of a nonwoven layer is related to the pore structure (while under a load) of the nonwoven layer. As will be discussed in greater detail below, it is often desired that the nonwoven layer have a relatively high degree of wet resilience.

The pore structure (while under a load) of a fibrous structure formed from fibers of a polymeric material will, as discussed above, relate to the wet and/or dry modulus of the constituent fibers. Wet modulus of the constituent fibers should be considered for fibers that may likely be wetted during use. For the purposes of estimating the effect of load on the pore structure of a fibrous structure formed from fibers of a polymeric material the tensile modulus of the fiber which can be related to the flexural rigidity of the fiber as shown in the monograph "Physical Properties of Textile Fibers", W. E. Morton and J. W. S. Hearl, The Textile Institute, 1975, can be used.

As a general rule, the polymeric materials from which the synthetic polymeric fibers of the nonwoven layer are formed will be inherently hydrophobic. As used herein, a polymeric material will be considered to be "inherently" hydrophobic or hydrophilic when the polymeric material, free from any surface modifications or treatments, e.g., surface active agents, spin finishes, blooming agents, etc., is hydrophobic or hydrophilic, respectively.

When the synthetic polymeric fibers of the nonwoven layer are formed from a polymeric material which is inherently hydrophobic, it is often desirable to treat the fibers with a surface modifying material to render the surface of the fiber hydrophilic. For example, a surfactant may be applied to the fibers.

The nonwoven layer may also comprise hydrophilic fibers. The hydrophilic materials may be inherently hydrophilic such as cellulosic fibers such as wood pulp fluff, cotton linters, and the like, regenerated cellulose fibers such as rayon, or certain nylon copolymers such as poly (pentamethylenecarbonamide) (nylon-6)/polyethylene oxide. Alternatively, the hydrophilic fibers may be hydrophobic fibers which have been treated to possess a hydrophilic surface. For example, the fibers may be formed from a polyolefin material which is subsequently coated with a surface active agent such that the fiber itself is hydrophilic as described herein. Other methods of hydrophilizing fibers formed from hydrophobic materials are known and suited for use in the present invention.

Methods of providing inherently hydrophilic fibers such as wood pulp fluff are known. Hydrophobic fibers which can be treated to possess a hydrophilic surface are suitably formed by processes known to those skilled in the art. If the hydrophilic fibers are hydrophobic fibers which have been treated to possess a hydrophilic surface, the fibers will suitably have a fiber length and maximum cross-sectional dimension as set forth above. If the hydrophilic fibers are inherently hydrophilic such as wood pulp fluff, rayon, cotton, cotton linters and the like, the fibers will generally have a length of from about 1.0 to 50 mm and a maximum cross-sectional dimension of from about 0.5 to 100 µm.

The nonwoven layer suitably comprises preferably from about 10 to 100% by weight, more preferably from about 30 to 100% by weight, most preferably from about 55 to 100% by weight of hydrophilic fibers, preferably inherently hydrophilic fibers. In addition to the hydrophilic fibers, the nonwoven layer may contain from about 90 to 0% by weight of a high wet modulus, preferably inherently hydrophobic, fibers. The nonwoven layer may be formed from a single type of hydrophilic fiber or may contain hydrophilic fibers having different compositions, lengths and maximum cross-sectional dimensions.

In one preferred embodiment, the nonwoven layer is formed from air laid cellulosic fibers such as wood pulp fluff Wood pulp fluff fibers are preferred for use due to their ready availability and due to the fact that the fibers are relatively inexpensive compared to synthetic polymeric fibers.

The nonwoven layer suitably has a basis weight of preferably from about 10 to 200 gsm, more preferably from about 20 to 150 gsm, most preferably from about 25 to 125 gsm.

The nonwoven layer suitably has a density of preferably from about 0.04 to 0.20 $g/cm^3$, more preferably from about 0.06 to 0.16 $g/cm^3$, most preferably from about 0.08 to 0.14 $g/cm^3$.

Typically the fluid-absorbent cores may contain a single type of water-absorbent polymer particles or may contain water-absorbent polymer particles derived from different kinds of water-absorbent polymer material. Thus, it is possible to add water-absorbent polymer particles from a single kind of polymer material or a mixture of water-absorbent polymer particles from different kinds of polymer materials, e.g. a mixture of regular water-absorbent polymer particles, derived from gel polymerization with water-absorbent polymer particles, derived from dropletization polymerization. Alternatively it is possible to add water-absorbent polymer particles derived from inverse suspension polymerization.

Alternatively it is possible to mix water-absorbent polymer particles showing different feature profiles. Thus, the fluid-absorbent core may contain water-absorbent polymer particles with uniform pH value, or it may contain water-absorbent polymer particles with different pH values, e.g. two- or more component mixtures from water-absorbent polymer particles with a pH in the range from about 4.0 to about 7.0. Preferably, applied mixtures deriving from mixtures of water-absorbent polymer particles got from gel polymerization or inverse suspension polymerization with a pH in the range from about 4.0 to about 7.0 and water-absorbent polymer particles got from dropletization polymerization.

The fluid-absorbent core comprises at least 75% by weight, preferably at least 80% by weight, more preferably at least 83% by weight, most preferably at least 85% by weight, of water-absorbent polymer particles.

The quantity of water-absorbent polymer particles within the fluid-absorbent core is preferably from 3 to 20 g, more preferably from 6 to 14 g, most preferably from 8 to 12 g in the case of maxi-diapers, and in the case of incontinence products up to about 50 g.

The types of adhesives are not particularly limited. A wide variety of thermoplastic compositions are suitable for use as pressure sensitive adhesives in the present invention.

Thermoplastic compositions may comprise a single type of thermoplastic polymers or a blend of thermoplastic polymers. Alternatively, the thermoplastic composition may comprise hot melt adhesives comprising at least one thermoplastic polymer together with thermoplastic diluents such as tackifiers, plasticizers or other additives, e.g. antioxidants. The thermoplastic composition may further comprise pressure sensitive hot melt adhesives comprising e.g. crystalline polypropylene and an amorphous polyalphaolefine or styrene block copolymer and mixture of waxes.

Suitable thermoplastic polymers are styrenic block copolymers including A-B-A triblock segments, A-B diblock segments and $(A-B)_n$ radial block copolymer segments. The letter A designs non-elastomeric polymer segments, e.g. polystyrene, and B stands for unsaturated conjugated diene or their (partly) hydrogenated form. Preferably B comprises isoprene, butadiene, ethylene/butylene (hydrogenated butadiene), ethylene/propylene (hydrogenated isoprene) and mixtures thereof.

Other suitable thermoplastic polymers are amorphous polyolefins, amorphous polyalphaolefins and metallocene polyolefins.

The construction of the fluid-absorbent cores is made and controlled by the discrete application of adhesives as known to people skilled in the art. Examples would be e.g. Dispomelt 505B, Dispomelt Cool 1101, as well as other specific function adhesives manufactured by National Starch or Henkel.

Ultrathin fluid-absorbent cores are be formed by immobilization of water-absorbent polymer particles on a substrate layer using adhesives. Preferably the water-absorbent polymer particles form longitudinal strips or discrete spots. Other patterns of the water-absorbent polymer particles are also possible.

Typically, the water-absorbent polymer particles form a discontinuous layer on the substrate layer, i.e. a nonwoven layer, covered by a thermoplastic composition as adhesive forming discrete cavities, so that the water-absorbent polymer particles are immobilized.

It is also possible to use a second substrate layer that comprises an adhesive instead of the thermoplastic composition.

In a preferred embodiment the ultrathin fluid-absorbent cores comprise at least two layers of immobilized water-absorbent polymer particles.

Suitable fluid-absorbent cores may also include layers, which are formed by the process of manufacturing the fluid-absorbent article. The layered structure may be formed by subsequently generating the different layers in z-direction.

Alternatively a core-structure can be formed from two or more preformed layers to get a layered fluid-absorbent core. These uniform or different layers can be fixed to each other at their adjacent plane surfaces. Alternatively, the layers may be combined in a way that a plurality of chambers is formed, in which separately water-absorbent polymer material is incorporated.

Further a composite structure can be formed from a carrier layer (e.g. a polymer film), onto which the water-absorbent polymer material is affixed. The fixation can be done at one side or at both sides. The carrier layer may be pervious or impervious for body-fluids.

Typically fluid-absorbent articles comprising at least an upper liquid-pervious layer (A), at least a lower liquid-impervious layer (B) and at least one fluid-absorbent core between the layer (A) and the layer (B) besides other optional layers. The addition of a second fluid-absorbent core to the first fluid-absorbent core offers more possibilities in body fluid transfer and distribution. Moreover higher quantities of discharged body fluids can be retained. Having the opportunity of combining several layers showing different water-absorbent polymer concentration and content, it is possible to reduce the thickness of the fluid-absorbent article to a minimum even if there are several fluid-absorbent cores included.

Suitable fluid-absorbent articles are including single or multi-core systems in any combination with other layers which are typically found in fluid-absorbent articles. Preferred fluid-absorbent articles include single- or double-core systems; most preferably fluid-absorbent articles include a single fluid-absorbent core.

The fluid-absorbent core typically has a uniform size or profile. Suitable fluid-absorbent cores can also have profiled structures, concerning the shape of the core and/or the content of water-absorbent polymer particles and/or the distribution of the water-absorbent polymer particles and/or the dimensions of the different layers if a layered fluid-absorbent core is present.

These layers or foldings are preferably joined to each e.g. by addition of adhesives or by mechanical, thermal or ultrasonic bonding or combinations thereof. Water-absorbent polymer particles may be comprised within or between the individual layers, e.g. by forming separate water-absorbent polymer-layers.

The fluid-absorbent core may comprise additional additives typically present in fluid-absorbent articles known in the art. Exemplary additives are odor control additives and wetness indication additives.

Concerning odor control, perfumes and/or odor control additives are optionally added. Suitable odor control additives are all substances of reducing odor developed in carrying fluid-absorbent articles over time known in the art. Thus, suitable odor control additives are inorganic materials, such as zeolites, activated carbon, bentonite, silica, aerosile, kieselguhr, clay; chelants such as ethylenediamine tetraacetic acid (EDTA), cyclodextrins, aminopolycarbonic acids, ethylenediamine tetramethylene phosphonic acid, aminophosphate, polyfunctional aromates, N,N-disuccinic acid.

Suitable odor control additives are further antimicrobial agents such as quaternary ammonium, phenolic, amide and nitro compounds and mixtures thereof; bactericides such as silver salts, zinc salts, cetylpyridinium chloride and/or triclosan as well as surfactants having an HLB value of less than 12.

Suitable odor control additives are further compounds with anhydride groups such as maleic-, itaconic-, polymaleic- or polyitaconic anhydride, copolymers of maleic acid with C2-C8 olefins or styrene, polymaleic anhydride or copolymers of maleic anhydride with isobutene, di-isobutene or styrene, compounds with acid groups such as ascorbic, benzoic, citric, salicylic or sorbic acid and fluid-soluble polymers of monomers with acid groups, homo- or co-polymers of C3-05 mono-unsaturated carboxylic acids.

Suitable odor control additives are further perfumes such as allyl caproate, allyl cyclohexaneacetate, allyl cyclohexanepropionate, allyl heptanoate, amyl acetate, amyl propionate, anethol, anixic aldehyde, anisole, benzaldehyde, benzyl acetete, benzyl acetone, benzyl alcohole, benzyl butyrate, benzyl formate, camphene, camphor gum, laevo-carveol, cinnamyl formate, cis-jasmone, citral, citronellol and its derivatives, cuminic alcohol and its derivatives, cyclal C, dimethyl benzyl carbinol and its derivatives, dimethyl octanol and its derivatives, eucalyptol, geranyl derivatives, lavandulyl acetete, ligustral, d-limonene, linalool, linalyl derivatives, menthone and its derivatives, myrcene and its derivatives, neral, nerol, p-cresol, p-cymene, orange terpenes, alpha-ponene, 4-terpineol, thymol etc.

Masking agents are also used as odor control additives. Masking agents are in solid wall material encapsulated perfumes. Preferably, the wall material comprises a fluid-soluble cellular matrix which is used for time-delay release of the perfume ingredient.

Further suitable odor control additives are transition metals such as Cu, Ag, and Zn, enzymes such as urease-inhibitors, starch, pH buffering material, chitin, green tea plant extracts, ion exchange resin, carbonate, bicarbonate, phosphate, sulfate or mixtures thereof.

Preferred odor control additives are green tea plant extracts, silica, zeolite, carbon, starch, chelating agent, pH buffering material, chitin, kieselguhr, clay, ion exchange resin, carbonate, bicarbonate, phosphate, sulfate, masking agent or mixtures thereof. Suitable concentrations of odor control additives are from about 0.5 to about 300 gsm.

Newest developments propose the addition of wetness indication additives. Besides electrical monitoring the wetness in the fluid-absorbent article, wetness indication additives comprising a hot melt adhesive with a wetness indicator are known. The wetness indication additive changes the colour from yellow to a relatively dark and deep blue. This colour change is readily perceivable through the liquid-impervious outer material of the fluid-absorbent article. Existing wetness indication is also achieved via application of water soluble ink patterned on the backsheet which disappears when wet.

Suitable wetness indication additives comprising a mixture of sorbitan monooleate and polyethoxylated hydrogenated castor oil. Preferably, the amount of the wetness indication additive is in the range of about 1 to 5% by weight related to the weight of the fluid-absorbent core.

The basis weight of the fluid-absorbent core is preferably in the range of 400 to 1200 gsm. The density of the fluid-absorbent core is preferably in the range of 0.1 to 0.50 g/cm3. The thickness of the fluid-absorbent core is in the case of diapers preferably in the range of 1 to 5 mm, in the case of incontinence products preferably in the range of 3 to 15 mm.

Optional Acquisition-Distribution Layer (D)

An optional acquisition-distribution layer (D) is located between the upper layer (A) and the fluid-absorbent core (C)

and is preferably constructed to efficiently acquire discharged body fluids and to transfer and distribute them to other regions of the fluid-absorbent composition or to other layers, where the body fluids are immobilized and stored. Thus, the upper layer transfers the discharged liquid to the acquisition-distribution layer (D) for distributing it to the fluid-absorbent core.

The acquisition-distribution layer comprises fibrous material and optionally water-absorbent polymer particles.

The fibrous material may be hydrophilic, hydrophobic or can be a combination of both hydrophilic and hydrophobic fibers. It may be derived from natural fibers, synthetic fibers or a combination of both.

Suitable acquisition-distribution layers are formed from cellulosic fibers and/or modified cellulosic fibers and/or synthetics or combinations thereof Thus, suitable acquisition-distribution layers may contain cellulosic fibers, in particular wood pulp fluff Examples of further suitable hydrophilic, hydrophobic fibers, as well as modified or unmodified natural fibers are given in the chapter "Liquid-pervious Layer (A)" above.

Especially for providing both fluid acquisition and distribution properties, the use of modified cellulosic fibers is preferred. Examples for modified cellulosic fibers are chemically treated cellulosic fibers, especially chemically stiffened cellulosic fibers. The term "chemically stiffened cellulosic fibers" means cellulosic fibers that have been stiffened by chemical means to increase the stiffness of the fibers. Such means include the addition of chemical stiffening agent in the form of coatings and impregnates. Suitable polymeric stiffening agents can include: cationic modified starches having nitrogen-containing groups, latexes, wet strength resins such as polyamide-epichlorohydrin resin, polyacrylamide, urea formaldehyde and melamine formaldehyde resins and polyethylenimine resins.

Stiffening may also include altering the chemical structure, e.g. by crosslinking polymer chains. Thus crosslinking agents can be applied to the fibers that are caused to chemically form intrafiber crosslink bonds. Further cellulosic fibers may be stiffened by cross-link bonds in individualized form. Suitable chemical stiffening agents are typically monomeric crosslinking agents including $C_2$-$C_8$ dialdehyde, $C_2$-$C_8$ monoaldehyde having an acid functionality, and especially $C_2$-$C_9$ polycarboxylic acids.

Preferably the modified cellulosic fibers are chemically treated cellulosic fibers. Especially preferred are curly fibers which can be obtained by treating cellulosic fibers with citric acid. Preferably the basis weight of cellulosic fibers and modified cellulosic fibers is from 50 to 200 gsm.

Suitable acquisition-distribution layers further include synthetic fibers. Known examples of synthetic fibers are found in the Chapter "Liquid-pervious Layer (A)" above. 3D-poly-ethylene in the function of acquisition-distribution layer is preferred.

Further, as in the case of cellulosic fibers, hydrophilic synthetic fibers are preferred. Hydrophilic synthetic fibers may be obtained by chemical modification of hydrophobic fibers. Preferably, hydrophilization is carried out by surfactant treatment of hydrophobic fibers. Thus the surface of the hydrophobic fiber can be rendered hydrophilic by treatment with a nonionic or ionic surfactant, e.g., by spraying the fiber with a surfactant or by dipping the fiber into a surfactant. Further preferred are permanent hydrophilic synthetic fibers.

The fibrous material of the acquisition-distribution layer may be fixed to increase the strength and the integrity of the layer. Technologies for consolidating fibers in a web are mechanical bonding, thermal bonding and chemical bonding. Detailed description of the different methods of increasing the integrity of the web is given in the Chapter "Liquid-pervious Layer (A)" above.

Preferred acquisition-distribution layers comprise fibrous material and water-absorbent polymer particles distributed within. The water-absorbent polymer particles may be added during the process of forming the layer from loose fibers, or, alternatively, it is possible to add monomer solution after the formation of the layer and polymerize the coating solution by means of UV-induced polymerization technologies. Thus, "in situ"-polymerization is a further method for the application of water-absorbent polymers.

Thus, suitable acquisition-distribution layers comprising from 80 to 100% by weight fibrous material and from 0 to 20% by weight water-absorbent polymer particles; preferably from 85 to 99.9% by weight fibrous material and from 0.1 to 15% by weight water-absorbent polymer particles; more preferably from 90 to 99.5% by weight fibrous material and from 0.5 to 10% by weight water-absorbent polymer particles; and most preferably from 95 to 99% by weight fibrous material and from 1 to 5% by weight water-absorbent polymer particles.

Preferred acquisition-distribution layers show basis weights in the range from 20 to 200 gsm, most preferred in the range from 40 to 50 gsm, depending on the concentration of water-absorbent polymer particles.

Optional Tissue Layer (E)

An optional tissue layer is disposed immediately above and/or below (C).

The material of the tissue layer may comprise any known type of substrate, including webs, garments, textiles and films. The tissue layer may comprise natural fibers, such as cellulose, cotton, flax, linen, hemp, wool, silk, fur, hair and naturally occurring mineral fibers. The tissue layer may also comprise synthetic fibers such as rayon and lyocell (derived from cellulose), polysaccharides (starch), polyolefin fibers (polypropylene, polyethylene), polyamides, polyester, butadiene-styrene block copolymers, polyurethane and combinations thereof Preferably, the tissue layer comprises cellulose fibers.

Other Optional Components (F)

1. Leg Cuff

Typical leg cuffs comprising nonwoven materials which can be formed by direct extrusion processes during which the fibers and the nonwoven materials are formed at the same time, or by laying processes of preformed fibers which can be laid into nonwoven materials at a later point of time. Examples for direct extrusion processes include spunbonding, meltblowing, solvent spinning, electrospinning and combinations thereof. Examples of laying processes include wet-laying and dry-laying (e.g. air-laying, carding) methods. Combinations of the processes above include spunbond-meltblown-spunbond (sms), spunbond-meltblow-melt-blown-spunbond (smms), spunbond-carded (sc), spunbond-airlaid (sa), meltblown-airlaid (ma) and combinations thereof. The combinations including direct extrusion can be combined at the same point in time or at a subsequent point in time. In the examples above, one or more individual layers can be produced by each process. Thus, "sms" means a three layer nonwoven material, "smsms" or "ssmms" means a five layer nonwoven material. Usually, small type letters (sms) designate individual layers, whereas capital letters (SMS) designate the compilation of similar adjacent layers.

Further, suitable leg cuffs are provided with elastic strands. Preferred are leg cuffs from synthetic fibers showing the layer combinations sms, smms or smsms. Preferred are nonwovens with the density of 13 to 17 gsm. Preferably leg cuffs are provided with two elastic strands.

2. Elastics

The elastics are used for securely holding and flexibly closing the fluid-absorbent article around the wearer's body, e.g. the waist and the legs to improve containment and fit. Leg elastics are placed between the outer and inner layers or the fluid-absorbent article, or between the outer cover and the bodyside liner. Suitable elastics comprising sheets, ribbons or strands of thermoplastic polyurethane, elastomeric materials, poly(ether-amide) block copolymers, thermoplastic rubbers, styrene-butadiene copolymers, silicon rubbers, natural rubbers, synthetic rubbers, styrene isoprene copolymers, styrene ethylene butylene copolymers, nylon copolymers, spandex fibers comprising segmented polyurethane and/or ethylene-vinyl acetate copolymer. The elastics may be secured to a substrate after being stretched, or secured to a stretched substrate. Otherwise, the elastics may be secured to a substrate and then elastisized or shrunk, e.g. by the application of heat.

3. Closing System

The closing system includes tape tabs, landing zone, elastomerics, pull ups and the belt system.

At least a part of the first waist region is attached to a part of the second waist region by the closing system to hold the fluid-absorbent article in place and to form leg openings and the waist of the fluid-absorbent article. Preferably the fluid-absorbent article is provided with a re-closable closing system.

The closing system is either re-sealable or permanent, including any material suitable for such a use, e.g. plastics, elastics, films, foams, nonwoven substrates, woven substrates, paper, tissue, laminates, fiber reinforced plastics and the like, or combinations thereof. Preferably the closing system includes flexible materials and works smooth and softly without irritating the wearer's skin.

One part of the closing elements is an adhesive tape, or comprises a pair of laterally extending tabs disposed on the lateral edges of the first waist region. Tape tabs are typically attached to the front body panel and extend laterally from each corner of the first waistband. These tape tabs include an adhesive inwardly facing surface which is typically protected prior to use by a thin, removable cover sheet.

Suitable tape tabs may be formed of thermoplastic polymers such as polyethylene, polyurethane, polystyrene, polycarbonate, polyester, ethylene vinyl acetate, ethylene vinyl alcohol, ethylene vinyl acetate acrylate or ethylene acrylic acid copolymers.

Suitable closing systems comprise further a hook portion of a hook and loop fastener and the target devices comprise the loop portion of a hook and loop fastener.

Suitable mechanical closing systems including a landing zone. Mechanical closing systems may fasten directly into the outer cover. The landing zone may act as an area of the fluid-absorbent article into which it is desirable to engage the tape tabs. The landing zone may include a base material and a plurality of tape tabs. The tape tabs may be embedded in the base material of the landing zone. The base material may include a loop material. The loop material may include a backing material and a layer of a nonwoven spunbond web attacked to the backing material.

Thus suitable landing zones can be made by spunbonding. Spunbonded nonwovens are made from melt-spun fibers formed by extruding molten thermoplastic material. Preferred is bioriented polypropylene (BOPP), or brushed/closed loop in the case of mechanical closing systems.

Further, suitable mechanical closing systems including elastic units serving as a flexible waist band for fluid-absorbents articles, such as pants or pull-ups. The elastic units enabling the fluid-absorbent article to be pulled down by the wearer as e.g. a training pant.

Suitable pants-shaped fluid-absorbent article has front section, rear section, crotch section, side sections for connecting the front and rear sections in lateral direction, hip section, elastic waist region and liquid-tight outer layer. The hip section is arranged around the waist of the user. The disposable pants-shaped fluid-absorbent article (pull-up) has favorable flexibility, stretchability, leak-proof property and fit property, hence imparts excellent comfort to the wearer.

Suitable pull-ups comprising thermoplastic films, sheets and laminates having a low modulus, good tear strength and high elastic recovery.

Suitable closing systems may further comprise elastomerics for the production of elastic areas within the fastening devices of the fluid-absorbent article. Elastomerics provide a conformable fit of the fluid-absorbent article to the wearer at the waist and leg openings, while maintaining adequate performance against leakage.

Suitable elastomerics are elastomeric polymers or elastic adhesive materials showing vapor permeability and liquid barrier properties. Preferred elastomerics are retractable after elongation to a length equivalent to its original length.

Suitable closing systems further comprise a belt system, comprising waist-belt and leg-belts for flexibly securing the fluid-absorbent article on the body of the wearer and to provide an improved fit on the wearer. Suitable waist-belts comprising two elastic belts, a left elastic belt, and a right elastic belt. The left elastic belt is associated with each of the left angular edges. The right elastic belt associated with each of the right angular edges. The left and right side belts are elastically extended when the absorbent garment is laid flat. Each belt is connected to and extends between the front and rear of the fluid-absorbent article to form a waist hole and leg holes.

Preferably the belt system is made of elastomerics, thus providing a conformable fit of the fluid-absorbent article and maintaining adequate performance against leakage.

D. Fluid-Absorbent Article Construction

The present invention further relates to the joining of the components and layers, films, sheets, tissues or substrates mentioned above to provide the fluid-absorbent article. At least two, preferably all layers, films, sheets, tissues or substrates are joined.

Suitable fluid-absorbent articles include a single- or multiple fluid-absorbent core-system. Preferably fluid-absorbent articles include a single- or double fluid-absorbent core-system.

Suitable fluid-storage layers of the fluid-absorbent core comprising homogenous or inhomogeneous mixtures of fibrous materials comprising water-absorbent polymer particles homogeneously or inhomogeneously dispersed in it. Suitable fluid-storage layers of the fluid-absorbent core including a layered fluid-absorbent core-system comprising homogenous mixtures of fibrous materials and optionally comprising water-absorbent polymer particles, whereby each of the layers may be prepared from any fibrous material by means known in the art.

In order to immobilize the water-absorbent polymer particles, the adjacent layers are fixed by the means of thermoplastic materials, thereby building connections throughout the whole surface or alternatively in discrete areas of junction. For the latter case, cavities or pockets are built carrying the fluid-absorbent particles. The areas of junction may have a regular or irregular pattern, e.g. aligned with the longitudinal axis of the fluid-absorbent core or in a pattern of polygons, e.g. pentagons or hexagons. The areas of junction itself may be of rectangular, circular or squared shape with diameters between about 0.5 mm and 2 mm. Fluid-absorbent articles comprising areas of junction show a better wet strength.

The construction of the products chassis and the components contained therein is made and controlled by the discrete application of hotmelt adhesives as known to people skilled in the art. Examples would be e.g. Dispomelt 505B, Dispomelt Cool 1101, as well as other specific function adhesives manufactured by National Starch or Henkel.

The water-absorbent polymer particles and the fluid-absorbent articles are tested by means of the test methods described below.

METHODS

The measurements should, unless stated otherwise, be carried out at an ambient temperature of 23±2° C. and a relative atmospheric humidity of 50±10%. The water-absorbent polymers are mixed thoroughly before the measurement.

Saline Flow Conductivity (SFC)

Figure 8:
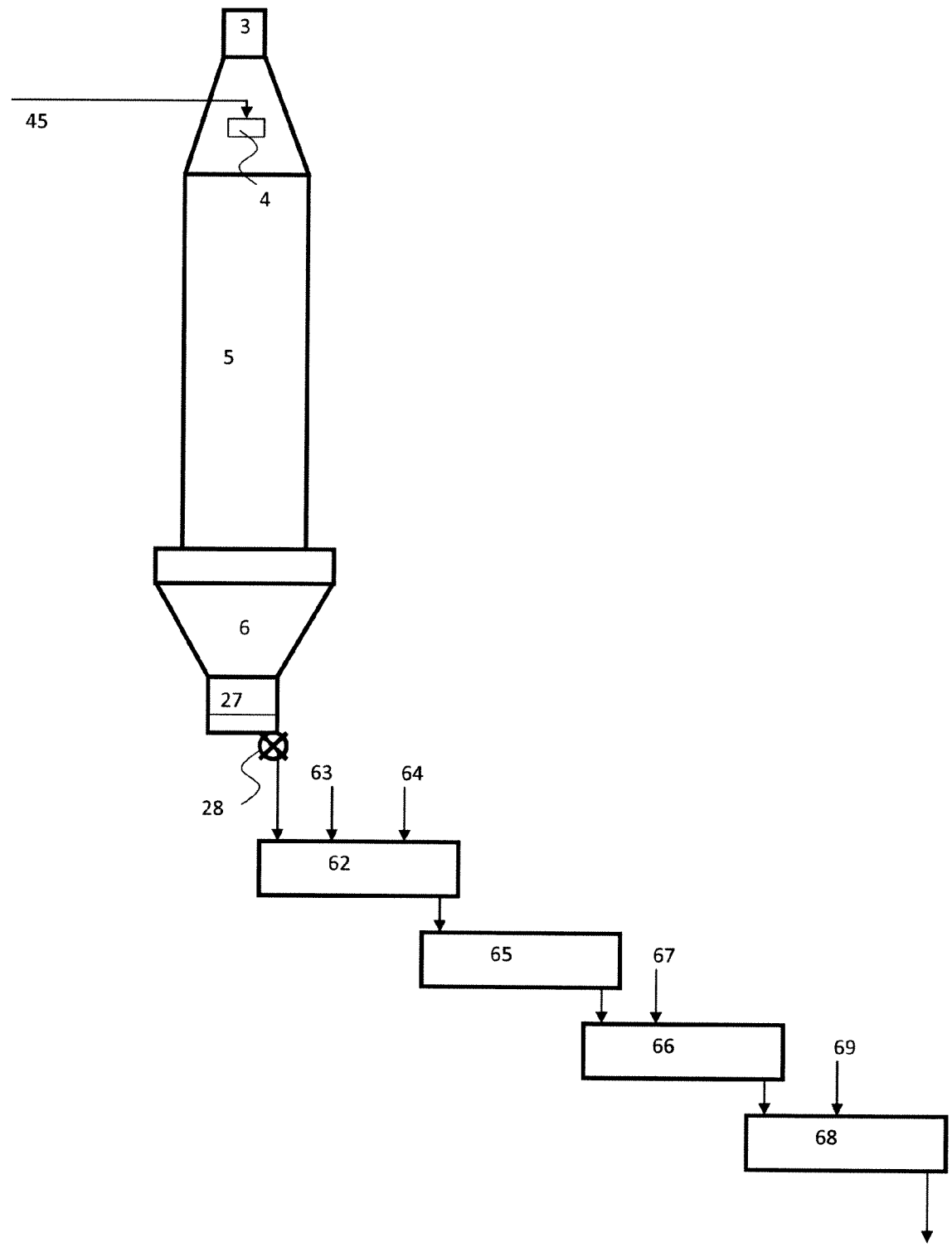
FIG. 8 illustrates a process scheme (external thermal post-treatment and postcrosslinking)

The saline flow conductivity is, as described in EP 0 640 330 A1, determined as the gel layer permeability of a swollen gel layer of water-absorbent polymer particles, although the apparatus described on page 19 and in FIG. 8 in the aforementioned patent application was modified to the effect that the glass frit (40) is no longer used, the plunger (39) consists of the same polymer material as the cylinder (37) and now comprises 21 bores having a diameter of 9.65 mm each distributed uniformly over the entire contact surface. The procedure and the evaluation of the measurement remains unchanged from EP 0 640 330 A1. The flow rate is recorded automatically.

The saline flow conductivity (SFC) is calculated as follows:

SFC [cm$^3$ s/g]=$(Fg(t=0) \times L0)/(d \times A \times WP)$, where Fg(t=0) is the flow rate of NaCl solution in g/s, which is obtained by means of a linear regression analysis of the Fg(t) data of the flow determinations by extrapolation to t=0, L0 is the thickness of the gel layer in cm, d is the density of the NaCl solution in g/cm$^3$, A is the surface area of the gel layer in cm$^2$ and WP is the hydrostatic pressure over the gel layer in dyn/cm$^2$.

Free Swell Rate (FSR)

1.00 g (=W1) of the dry water-absorbent polymer particles is weighed into a 25 ml glass beaker and is uniformly distributed on the base of the glass beaker. 20 ml of a 0.9% by weight sodium chloride solution are then dispensed into a second glass beaker, the content of this beaker is rapidly added to the first beaker and a stopwatch is started. As soon as the last drop of salt solution is absorbed, confirmed by the disappearance of the reflection on the liquid surface, the stopwatch is stopped. The exact amount of liquid poured from the second beaker and absorbed by the polymer in the first beaker is accurately determined by weighing back the second beaker (=W2). The time needed for the absorption, which was measured with the stopwatch, is denoted t. The disappearance of the last drop of liquid on the surface is defined as time t.

The free swell rate (FSR) is calculated as follows:

FSR [g/gs]=$W2/(W1 \times t)$

When the moisture content of the hydrogel-forming polymer is more than 3% by weight, however, the weight W1 must be corrected for this moisture content.

Vortex 50.0±1.0 ml of 0.9% NaCl solution are added into a 100 ml beaker. A cylindrical stirrer bar (30×6 mm) is added and the saline solution is stirred on a stir plate at 60 rpm. 2.000±0.010 g of water-absorbent polymer particles are added to the beaker as quickly as possible, starting a stop watch as addition begins. The stopwatch is stopped when the surface of the mixture becomes "still" that means the surface has no turbulence, and while the mixture may still turn, the entire surface of particles turns as a unit. The displayed time of the stopwatch is recorded as Vortex time.

Morphology

Particle morphologies of the water-absorbent polymer particles were investigated in the swollen state by microscope analysis. Approximately 100 mg of the water-absorbent polymer particles were placed on a glass microscope slide. With a syringe, 0.9% aqueous NaCl solution was placed on the water-absorbent polymer particles to swell them. Solution was constantly refilled as it was absorbed by the particles. Care has to be taken that the water-absorbent polymer particles do not run dry. After 30 min swelling time, the slide was put under the microscope (Leica Macroscope Z16 APO, magnification 20×, backlighting by a Schott KL2500 LCD cold light source, camera Leica DFC 420, all by Leica Microsysteme Vein ieb GmbH; Wetzlar; Germany) and 3 pictures were taken at different parts of the sample.

Morphologies can be divided into there categories: Type 1 are particles with one cavity having diameters from 0.4 to 2.5 mm, Type 2 are particles with more than one cavity having diameters from 0.001 to 0.3 mm, and Type 3 are solid particles with no visible cavity.

Figure 9:
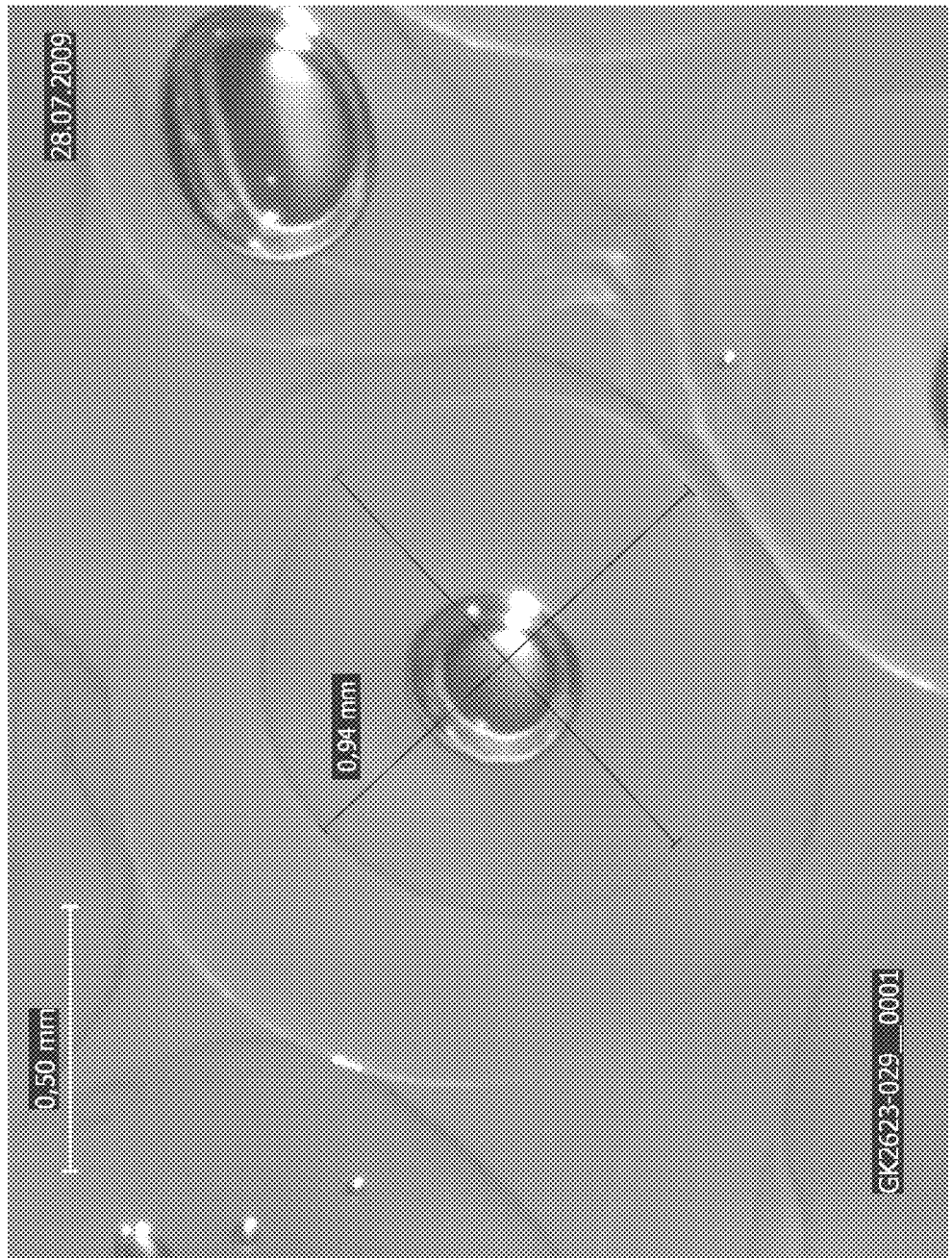
FIG. 9 shows a swollen particle of type 1 with a cavity having a diameter of 0.94 mm.
Figure 10:
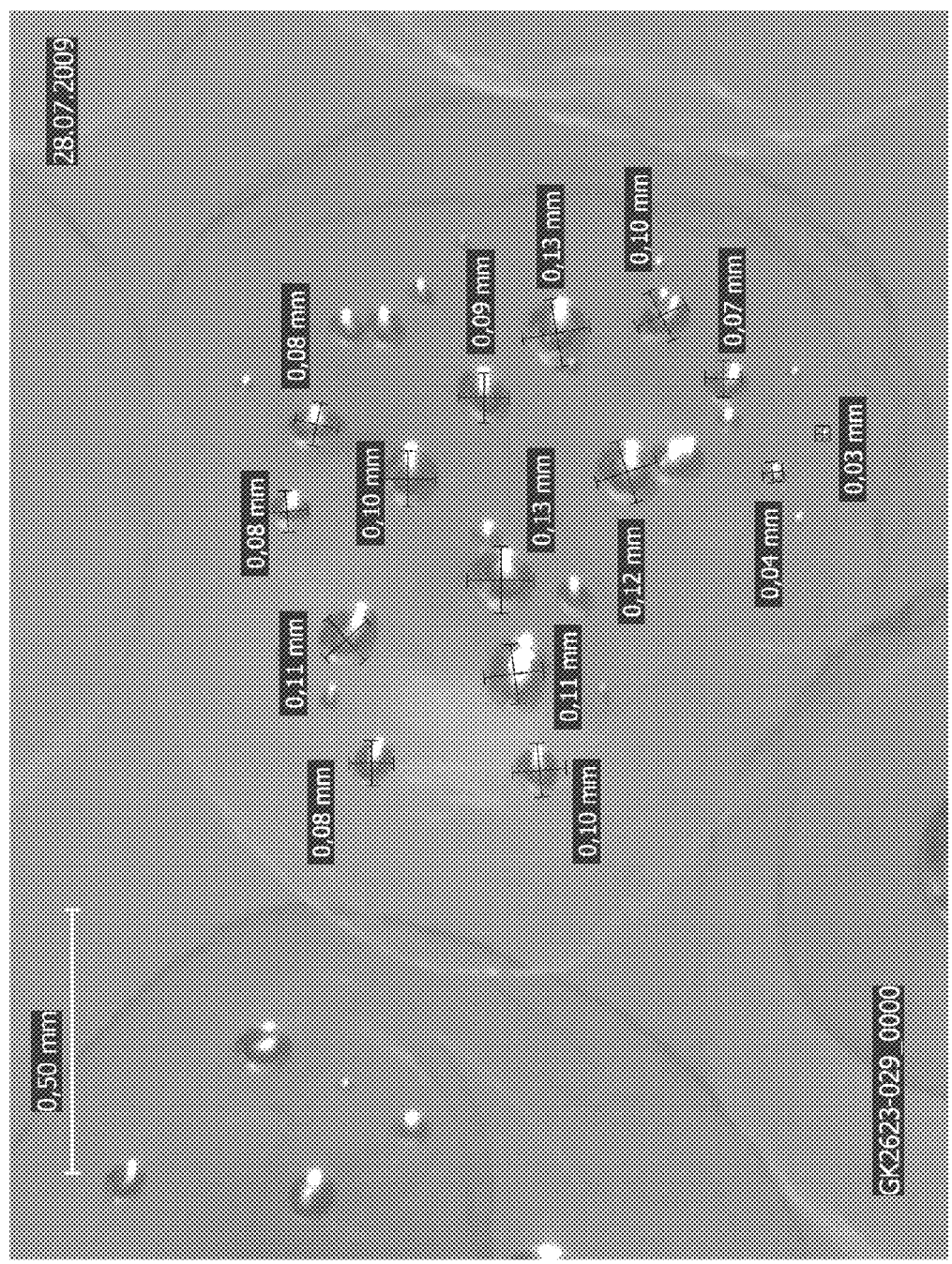
FIG. 10 shows a swollen particle of type 2 with more than 15 cavities having diameters from less than 0.03 to 0.13 mm.

FIG. 9 shows a swollen particle of type 1 with a cavity having a diameter of 0.94 mm and FIG. 10 shows a swollen particle of type 2 with more than 15 cavities having diameters from less than 0.03 to 0.13 mm.

The photograph is analyzed and the numbers of each category is recorded. Undefined or agglomerated particles are omitted from further evaluation. The individual results of the three photographs of each sample are averaged.

Free Swell Gel Bed Permeability (GBP)

The method to determine the free swell gel bed permeability is described in US 2005/0256757, paragraphs [0061] to [0075].

Particle Size Distribution

The particle size distribution of the water-absorbent polymer particles is determined with the Camziser® image analysis system (Retsch Technology GmbH; Haan; Germany).

For determination of the average particle diameter and the particle diameter distribution the proportions of the particle fractions by volume are plotted in cumulated form and the average particle diameter is determined graphically.

The average particle diameter (APD) here is the value of the mesh size which gives rise to a cumulative 50% by weight.

The particle diameter distribution (PDD) is calculated as follows:

$$PDD = \frac{x_2 - x_1}{APD},$$

wherein $x_1$ is the value of the mesh size which gives rise to a cumulative 90% by weight and $x_2$ is the value of the mesh size which gives rise to a cumulative 10% by weight.

Mean Sphericity

The mean sphericity is determined with the Camziser® image analysis system (Retsch Technology GmbH; Haan; Germany) using the particle diameter fraction from 100 to 1,000 µm.

Moisture Content

The moisture content of the water-absorbent polymer particles is determined by the EDANA recommended test method No. WSP 230.2-05 "Moisture Content".

Centrifuge Retention Capacity (CRC)

The centrifuge retention capacity of the water-absorbent polymer particles is determined by the EDANA recommended test method No. WSP 241.2-05 "Centrifuge Retention Capacity", wherein for higher values of the centrifuge retention capacity lager tea bags have to be used.

Absorbency Under High Load (AUHL)

The absorbency under high load of the water-absorbent polymer particles is determined analogously to the EDANA recommended test method No. WSP 242.2-05 "Absorption Under Pressure", except using a weight of 49.2 g/cm$^2$ instead of a weight of 21.0 g/cm$^2$.

Extractables

The level of extractable constituents in the water-absorbent polymer particles is determined by the EDANA recommended test method No. WSP 270.2-05 "Extractables".

Wet SAP Shake Out (SAPLoss)

The wet SAP shake out of water-absorbent polymer particles is determined using a rectangle core sample having a size of 7 inch×4 inch (17.8 cm×10.2 cm) that is cut from the center of a fluid-absorbent core. The weight of the cut core sample is recorded as Dry Weight ($W_{dry}$). The dry core sample is laid in a pan and 10 g of 0.9% NaCl solution per gram of Dry Weight are added to the core sample homogeneously. Five minutes after all free liquid has been absorbed by the core sample, the wet core sample is weighted and recorded as Before Shake Wet Weight ($W_{b-wet}$). The wet core sample is carefully placed on top of an 850 micron U.S.A. standard testing sieve (VWR International LLC; Arlington Heights; U.S.A.). The sieve with the wet core sample is installed on a Retsch® AS 200 sieve shaker (Retsch GmbH; Haan; Gemany) and shaken at a pre-set amplitude of 2.00 for 5 minutes. Next, the wet core sample is picked up on the short end and vertically transferred to a weighting pan. The wet core sample is recorded as After Shake Wet Weight ($W_{a-wet}$). The wet SAP shake out (SAPLoss) is calculated as follows:

$$SAPLoss[\text{wt.\%}] = \frac{W_{b-wet} - W_{a-wet}}{W_{b-wet}}$$

The EDANA test methods are obtainable, for example, from the EDANA, Avenue Eugene Plasky 157, B-1030 Brussels, Belgium.

EXAMPLES

Preparation of the Base Polymer

Example 1

The process was performed in a cocurrent spray drying plant with an integrated fluidized bed (27) and an external fluidized bed (29) as shown in FIG. 1. The cylindrical part of the spray dryer (5) had a height of 22 m and a diameter of 3.4 m. The internal fluidized bed (IFB) had a diameter of 2.0 m and a weir height of 0.4 m. The external fluidized bed (EFB) had a length of 3.0 m, a width of 0.65 m and a weir height of 0.5 m.

The drying gas was feed via a gas distributor (3) at the top of the spray dryer. The drying gas was partly recycled (drying gas loop) via a baghouse filter (9) and a condenser column (12). The drying gas was nitrogen that comprises from 1% to 5% by volume of residual oxygen. Before start of polymerization the drying gas loop was filled with nitrogen until the residual oxygen was below 5% by volume. The gas velocity of the drying gas in the cylindrical part of the spray dryer (5) was 0.59 m/s. The pressure inside the spray dryer was 4 mbar below ambient pressure.

The spray dryer outlet temperature was measured at three points around the circumference at the end of the cylindrical part as shown in FIG. 3. Three single measurements (47) were used to calculate the average cylindrical spray dryer outlet temperature. The drying gas loop was heated up and the dosage of monomer solution is started up. From this time the spray dryer outlet temperature was controlled to 125° C. by adjusting the gas inlet temperature via the heat exchanger (20).

The product accumulated in the internal fluidized bed (27) until the weir height was reached. Conditioned internal fluidized bed gas having a temperature of 94° C. and a relative humidity of 38% was fed to the internal fluidized bed (27) via line (25). The relative humidity was controlled by adding steam via line (23). The gas velocity of the internal fluidized bed gas in the internal fluidized bed (27) was 0.8 m/s. The residence time of the product was 44 min.

The spray dryer offgas was filtered in baghouse filter (9) and sent to a condenser column (12) for quenching/cooling. Excess water was pumped out of the condenser column (12) by controlling the (constant) filling level inside the condenser column (12). The water inside the condenser column (12) was cooled by a heat exchanger (13) and pumped counter-current to the gas via quench nozzles (11) so that the temperature inside the condenser column (12) was 45° C. The water inside the condenser column (12) was set to an alkaline pH by dosing sodium hydroxide solution to wash out acrylic acid vapors.

The condenser column offgas was split to the drying gas inlet pipe (1) and the conditioned internal fluidized bed gas (25). The gas temperatures were controlled via heat exchangers (20) and (22). The hot drying gas was fed to the cocurrent spray dryer via gas distributor (3). The gas distributor (3) consists of a set of plates providing a pressure drop of 5 to 10 mbar depending on the drying gas amount.

The product was discharged from the internal fluidized bed (27) via rotary valve (28) into external fluidized bed (29). Conditioned external fluidized bed gas having a temperature of 55° C. was fed to the external fluidized bed (29) via line (40). The external fluidized bed gas was air. The gas velocity of the external fluidized bed gas in the external fluidized bed (29) was 0.8 m/s. The residence time of the product was 14 min.

The product was discharged from the external fluidized bed (29) via rotary valve (32) into sieve (33). The sieve (33) was used for sieving off overs/lumps having a particle diameter of more than 850 µm.

The monomer solution was prepared by mixing first acrylic acid with 3-tuply ethoxylated glycerol triacrylate (internal crosslinker) and secondly with 37.3% by weight sodium acrylate solution. The temperature of the resulting monomer solution was controlled to 10° C. by using a heat exchanger and pumping in a loop. A filter unit having a mesh size of 250 µm was used in the loop after the pump. The initiators were metered into the monomer solution upstream of the dropletizer by means of static mixers (41) and (42) via lines (43) and (44) as shown in FIG. 1. Sodium peroxodisulfate solution having a temperature of 20° C. was added via line (43) and 2,2'-azobis[2-(2-imidazolin-2-yl)pro-pane]dihydrochloride solution having a temperature of 5° C. was added via line (44). Each initiator was pumped in a loop and dosed via control valves to each dropletizer unit. A second filter unit having a mesh size of 100 μm was used after the static mixer (42). For dosing the monomer solution into the top of the spray dryer three dropletizer units were used as shown in FIG. 4.

A dropletizer unit consisted of an outer pipe (51) having an opening for the dropletizer cassette (53) as shown in FIG. 5. The dropletizer cassette (53) was connected with an inner pipe (52). The inner pipe (53) having a PTFE block (54) at the end as sealing can be pushed in and out of the outer pipe (51) during operation of the process for maintenance purposes.

The temperature of the dropletizer cassette (61) was controlled to 25° C. by water in flow channels (59) as shown in FIG. 6. The dropletizer cassette had 200 bores having a diameter of 200 μm and a bore separation of 15 mm. The dropletizer cassette (61) consisted of a flow channel (60) having essential no stagnant volume for homogeneous distribution of the premixed monomer and initiator solutions and two droplet plates (57). The droplet plates (57) had an angled configuration with an angle of 10°. Each droplet plate (57) was made of stainless steel and had a length of 500 mm, a width of 25 mm, and a thickness of 1 mm.

The feed to the spray dryer consisted of 10.25% by weight of acrylic acid 32.75% by weigh of sodium acrylate, 0.070% by weight of 3-tuply ethoxylated glycerol triacrylate (approx. 85% strength by weight), 0.12% by weight of 2,2'-azobis[2-(2-imidazolin-2-yl)-propane]dihydrochloride solution (15% by weigh in water), 0.12% by weight of sodium peroxodisulfate solution (15% by weight in water) and water. The degree of neutralization was 71%. The feed per bore was 2.0 kg/h.

The polymer particles exhibit the following features and absorption profile:
CRC of 31.0 g/g
SFC of $14\times10^{-7}$ cm$^3$ s/g
AUHL of 20.3 g/g
GBP of 5 Darcies
The resulting polymer particles had a particle diameter distribution of 0.55 and a mean sphericity of 0.92.

Example 2

Example 1 was repeated, except that the separation of the bores was 11 mm. For dosing the monomer solution into the top of the spray dryer three dropletizer unit with 267 bores having a diameter of 200 μm were used.

The conditioned internal fluidized bed gas had a temperature of 98° C. and a relative humidity of 45%.

The feed to the spray dryer consisted of 10.25% by weight of acrylic acid 32.75% by weigh of sodium acrylate, 0.039% by weight of 3-tuply ethoxylated glycerol triacrylate (approx. 85% strength by weight), 0.12% by weight of 2,2'-azobis[2-(2-imidazolin-2-yl)-propane]dihydrochloride solution (15% by weight in water), 0.12% by weight of sodium peroxodisulfate solution (15% by weight in water) and water. The feed per bore was 1.5 kg/h.

The polymer particles exhibit the following features and absorption profile:
CRC of 44.5 g/g
AUHL of 9.9 g/g
SFC of $1\times10^{-7}$ cm$^3$ s/g
The resulting polymer particles had a particle diameter distribution of 0.66 and a mean sphericity of 0.93.

Coating of the Base Polymer

Example 3

800 g of the water-absorbent polymer particles prepared in example 1 were added in a mechanical plough share mixer (Pflugschar® Mischer Typ M5; Gebr. Lödige Maschinenbau GmbH; Paderborn; Germany) at room temperature. At a stirring speed of 200 rpm, the water-absorbent polymer particles were coated with 3.8 by weight of aluminum sulfate solution (26.8% by weight in water) within 4 minutes. The speed of the mixer was reduced after coating to 60 rpm and the product was mixed for 5 more minutes at these conditions. After removal of the product from the mixer, it was sieved over an 850 μm screen to remove potential agglomerates.

The polymer particles exhibit the following features and absorption profile:
CRC of 31.0 g/g
SFC of $31\times10^{-7}$ cm$^3$ s/g
AUHL of 19.8 g/g
GBP of 60 Darcies
Moisture content of 11.7 wt. %

Postcrosslinking of the Base Polymer

Example 4

1 kg of the water-absorbent polymer particles prepared in example 2 were put into a laboratory ploughshare mixer with a heated jacket (model M 5; manufactured by Gebrüder Lödige Maschinenbau GmbH; Paderborn; Germany). A postcrosslinker solution was prepared by mixing 1.00 g of Denacol® EX 512 (polyglycerol polyglycidyl ether; obtained from Nagase ChemteX Corporation; Osaka; Japan), 7.5 g of propylene glycol, and 15 g of deionized water, into a beaker. At a mixer speed of 450 rpm, the postcrosslinker solution was added by a spray nozzle to the polymer powder over a three minute time period at room temperature. The mixer was then stopped, product sticking to the wall of the mixing vessel was scraped off (and re-united with the bulk), and mixing was continued for two more minutes at 450 rpm. The temperature of the product was then raised to 160° C. by heating the jacket of the mixer. The product was kept at this temperature for 15 minutes at a mixer speed of 80 rpm. After cooling down of the mixer, the product was discharged, sifted at 150 to 850 μm and characterized as follows:
CRC of 41.1 g/g
SFC of $7\times10^{-7}$ cm$^3$ s/g
AUHL of 29.3 g/g
Extractables of 3.2 wt. %
FSR of 0.21 g/gs
Vortex of 94.7 s Preparation of the Fluid-Absorbent Cores Example 5

A first substrate layer was laid on a flat cardboard and covered with a pattern template. The substrate was a commercially available 17 gsm forming tissue (Cellu Tissue Holdings, Inc.; East Hartford; U.S.A.) having a size of 14.5 inch× 4.5 inch (36.8 cm×11.4 cm).

The template was a commercially available stainless steel plate having square end slots and an open area of 40% (Direct Metals Company, LLC; Kennesaw; U.S.A.). The template had a size of 10 inch×14 inch (25.4 cm×35.6 cm). The slots had a size of ¼ inch×⅜ inch (0.64 cm×0.95 cm) and were side staggered having end and side bars of 3/16 inch (0.48 cm).

11 g of water-absorbent polymer particles prepared in example 3 were added as evenly as possible onto the template and then evenly distributed with a smooth rubber blade to create a pattern of water-absorbent polymer particles on the first substrate layer.

A piece of a commercially available pressure sensitive adhesive having 20 gsm (BASF Corporation; Monaca; U.S.A.) on a release paper was transferred onto a second substrate layer (corresponding to 0.84 g adhesive). Next, the template on the first substrate layer was carefully removed and the second substrate layer was placed on the top of the first substrate layer with the adhesive side of the second substrate layer facing the top side with the water-absorbent polymer particles of the first substrate layer.

The fluid-absorbent core was transferred with the cardboard into a Carver® Press model Auto Series 4425.4DI0A01 (Carver Inc.; Wabash; U.S.A.). The press was pre-set to 10,000 lbs (corresponding to 1,054 kPa) and immediately stopped once the pre-set pressure was reached.

The resulting fluid-absorbent core was analyzed, the results are summarized in table 1.

Example 6

Example 5 was repeated, except that the water-absorbent polymer particles prepared in example 4 were used. The resulting fluid-absorbent core was analyzed, the results are summarized in table 1.

Example 7

Example 5 was repeated, except that the substrate layers were commercially available 15 gsm nonwoven (AVGOL American Inc.; Mocksville; U.S.A.) having a size of 14.5 inch×4.5 inch (36.8 cm×11.4 cm). The resulting fluid-absorbent core was analyzed, the results are summarized in table 1.

Example 8

Example 7 was repeated, except that the water-absorbent polymer particles prepared in example 4 were used. The resulting fluid-absorbent core was analyzed, the results are summarized in table 1.

Example 9

Example 7 was repeated, except that the pattern template was a commercially available perforated plastic piece having round holes (United States Plastic Corporation; Lima Ohio; U.S.A.). The template had a size of 4.5 inch×14 inch (11.4 cm×35.6 cm) and a thickness of ⅛ inch (0.3 cm). The holes had a diameter of ¼ inch (0.64 cm) and were side staggered (every other hole was taped off) having end and side bars of ½ inch (1.3 cm). The resulting fluid-absorbent core was analyzed, the results are summarized in table 1.

Example 10

Example 9 was repeated, except that the water-absorbent polymer particles prepared in example 4 were used. The resulting fluid-absorbent core was analyzed, the results are summarized in table 1.

TABLE 1

Results of the wet SAP shake out procedure

| Example | water-absorbent polymer particles | substrate | pattern template | SAP Loss |
|---|---|---|---|---|
| Example 5 | Example 3 | tissue paper | square slots | 6.2 wt. % |
| Example 6 | Example 4 | tissue paper | square slots | 2.1 wt. % |
|  | ASAP® 531T | tissue paper | square slots | 65.2 wt. % |
|  | Hysorb® B7055 | tissue paper | square slots | 42.1 wt. % |
|  | Hysorb® T8760 | tissue paper | square slots | 17.5 wt. % |
| Example 7 | Example 3 | nonwoven | square slots | 6.4 wt. % |
| Example 8 | Example 4 | nonwoven | square slots | 4.8 wt. % |
|  | ASAP® 531T | nonwoven | square slots | 50.1 wt. % |
|  | Hysorb® B7055 | nonwoven | square slots | 47.2 wt. % |
|  | Hysorb® T8760 | nonwoven | square slots | 16.8 wt. % |
| Example 9 | Example 3 | nonwoven | round holes | 4.5 wt. % |
| Example 10 | Example 4 | nonwoven | round holes | 8.1 wt. % |
|  | ASAP® 531T | nonwoven | round holes | 31.3 wt. % |
|  | Hysorb® B7055 | nonwoven | round holes | 21.0 wt. % |
|  | Hysorb® T8760 | nonwoven | round holes | 13.6 wt. % |

ASAP® 531T, Hysorb® B7055, and Hysorb® T8760 are commercially available water-absorbent polymer particles (BASF SE; Ludwigshafen; Germany) prepared by customary solution polymerization.

The invention claimed is:

1. A fluid-absorbent core comprising a substrate layer, at least 75% by weight of water-absorbent polymer particles, and an adhesive, wherein the water-absorbent polymer particles have a mean sphericity from 0.86 to 0.99 and a wet SAP shake out of water-absorbent polymer particles out of the fluid-absorbent core is less than 10% by weight.

2. The fluid-absorbent core according to claim 1, wherein the fluid-absorbent core comprises at least 80% by weight of water-absorbent polymer particles.

3. The fluid-absorbent core according to claim 1, wherein the fluid-absorbent core comprises not more than 15% by weight of the adhesive.

4. The fluid-absorbent core according to claim 1, wherein the wet SAP shake out of water-absorbent polymer particles out of the fluid-absorbent core is less than 8% by weight.

5. The fluid-absorbent core according to claim 1, wherein the wet SAP shake out of water-absorbent polymer particles out of the fluid-absorbent core is less than 5% by weight.

6. The fluid-absorbent core according to claim 1, wherein the adhesive is a pressure sensitive adhesive.

7. The fluid-absorbent core according to claim 1, wherein the substrate layer is a nonwoven layer or a tissue paper.

8. The fluid-absorbent core according to claim 1, wherein the fluid-absorbent core comprises at least two layers of water-absorbent polymer particles.

9. The fluid-absorbent core according to claim 1, wherein the water-absorbent polymer particles are placed in discrete regions.

10. The fluid-absorbent core according to claim 1, wherein the water-absorbent polymer particles have a particle diameter distribution is less than 0.7.

11. The fluid-absorbent core according to claim 1, wherein a ratio of water-absorbent polymer particles having one cavity to water-absorbent polymer particles having more than one cavity is less than 1.0.

12. The fluid-absorbent core according to claim 1, wherein the water-absorbent polymer particles have a centrifuge retention capacity of at least 30 g/g, an absorption under high load of at least 15 g/g, and a saline flow conductivity of at least $5 \times 10^{-7}$ cm$^3$ s/g.

13. The fluid-absorbent core according to claim 1, wherein the water-absorbent polymer particles have a centrifuge retention capacity of at least 20 g/g, an absorption under high load of at least 15 g/g, and a saline flow conductivity of at least $80 \times 10^{-7}$ cm$^3$ s/g.

14. The fluid-absorbent core according to claim 1, wherein the water-absorbent polymer particles have a centrifuge retention capacity of at least 20 g/g and a free swell gel bed permeability of at least 20 Darcies.

\* \* \* \* \*